United States Patent
Aldiguier et al.

(10) Patent No.: US 11,248,204 B2
(45) Date of Patent: Feb. 15, 2022

(54) BIOLOGICALS AND THEIR USE IN PLANTS

(71) Applicant: DANISCO US INC., Palo Alto, CA (US)

(72) Inventors: Anne-Sophie Madeleine Elisabeth Aldiguier, San Carlos, CA (US); Jacob Andrew Latone, San Jose, CA (US); Nicolas Leiva, San Francisco, CA (US); Joshua Klaus Michel, San Bruno, CA (US); Aleksandra Virag, Cupertino, CA (US)

(73) Assignee: DANISCO US INC

( * ) Notice: Subject to any disclaimer, the term of this patent is extended or adjusted under 35 U.S.C. 154(b) by 351 days.

(21) Appl. No.: 16/301,997

(22) PCT Filed: Oct. 7, 2016

(86) PCT No.: PCT/US2016/055913
§ 371 (c)(1),
(2) Date: Nov. 15, 2018

(87) PCT Pub. No.: WO2017/200563
PCT Pub. Date: Nov. 23, 2017

(65) Prior Publication Data
US 2019/0281834 A1   Sep. 19, 2019

Related U.S. Application Data

(60) Provisional application No. 62/336,902, filed on May 16, 2016.

(51) Int. Cl.
*C12N 1/14* (2006.01)
*A01N 63/30* (2020.01)
*C12R 1/645* (2006.01)

(52) U.S. Cl.
CPC .............. *C12N 1/14* (2013.01); *A01N 63/30* (2020.01); *C12N 1/145* (2021.05); *C12R 2001/645* (2021.05)

(58) Field of Classification Search
None
See application file for complete search history.

(56) References Cited

U.S. PATENT DOCUMENTS

| | | |
|---|---|---|
| 5,360,607 A | 11/1994 | Eyal et al. |
| 7,951,388 B2 | 5/2011 | Stamets |
| 9,993,006 B2 * | 6/2018 | Bruck ................... A01N 43/36 |
| 2011/0038839 A1 | 2/2011 | Jackson et al. |
| 2012/0263690 A1 | 10/2012 | De Crecy |
| 2018/0325118 A1 | 11/2018 | Bisgaard-Frantzen et al. |

FOREIGN PATENT DOCUMENTS

| | | |
|---|---|---|
| EP | 1695625 A1 | 8/2006 |
| WO | 2004033624 A2 | 4/2004 |
| WO | 200937399 A2 | 3/2009 |
| WO | 2011022435 A2 | 2/2011 |
| WO | 2017144500 A1 | 8/2017 |

OTHER PUBLICATIONS

Gul, Hafiza Tahira et al: "Entomopathogenic Fungi as Effective Insect Pest Management Tactic: a Review", Applied Sciences and Business Economics, 2014, vol. 1, No. 1, pp. 10-18.
Hutwimmer, S et al: "Formation of Exudate Droplets by Metarhizium Anisopliae and the Presence of Destruxins", Mycologia, Jul. 27, 2009, vol. 102, No. 1, pp. 1-10.
Li, D.P. et al: Effects of Nutrients on Colony Formation, Growth, and Sporulation of Metarhizium Anisopliae (Deuteromycotina: Hyphomyceies), Journal of Invertebrate Pathology, May 1, 1995, vol. 65, No. 3, pp. 253-260.
St. Leger, R et al: "Germination Triggers of Metarhizium Anisopliae Conidia are Related to Host Species", Microbiology, Jul. 1, 1994, vol. 140, No. 7, pp. 1651-1660.
The International Search Report and Written Opinion of the International Searching Authority for PCT/US2016/055913, dated Oct. 2, 2017.
Rangel D E N et al: "Growth of Metarhizium Anisopliae on Non-Preferred Carbon Sources Yields Conidia With Increased UV-B Tolerance" Journal of Invertebrate Pathology, Oct. 1, 2006, col. 93, No. 2, pp. 127-134.

* cited by examiner

Primary Examiner — Robert J Yamasaki

(57) ABSTRACT

Entomopathogenic fungal strains, compositions, and methods and compositions of producing and using the strains for reducing overall insect damage.

12 Claims, 17 Drawing Sheets

Figure 1:
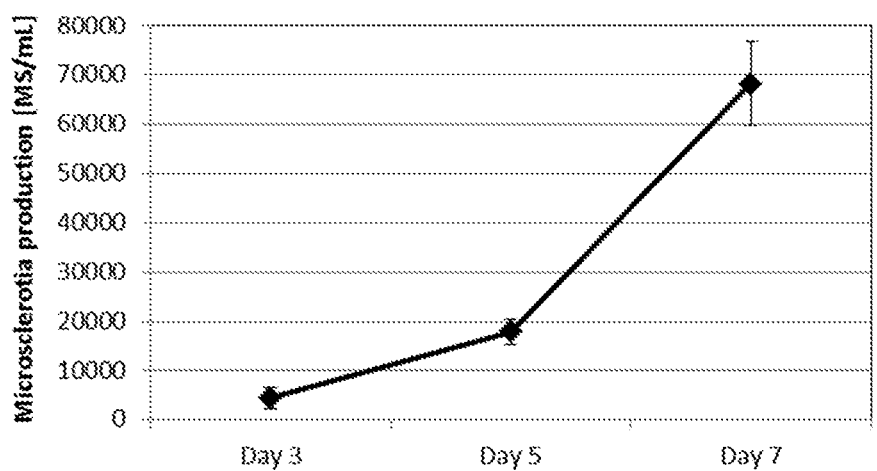
Figure 1:
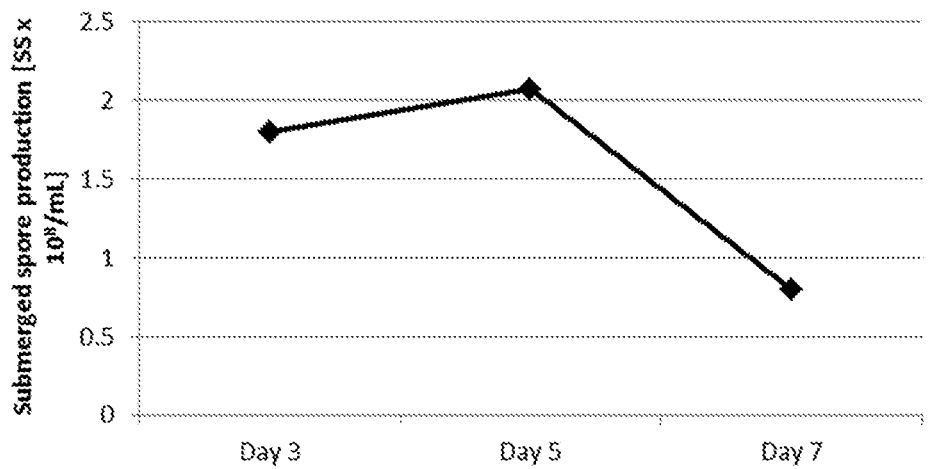

Submerged spore concentration profile for *Metarhizium anisopliae* strain 15013-1 ial Application-
BIOLOGICALS AND THEIR USE IN PLANTS

CROSS-REFERENCE TO RELATED APPLICATIONS

This application claims priority to International Application Number PCT/US2016/055913, filed Oct. 7, 2016, which claims priority to United States Provisional Application No. 62/336,902, filed May 16, 2016, which are hereby incorporated herein in their entireties by reference.

FIELD

Entomopathogenic fungal strains, compositions, and methods and compositions for producing and using entomopathogenic fungal strains for reducing overall insect damage.

BACKGROUND

There has been a long felt need for environmentally friendly compositions and methods for controlling or eradicating insect pests of agricultural significance, i.e., methods that are selective, environmentally inert, non-persistent, and biodegradable, and that fit well into insect pest management schemes. Furthermore, there is a need to produce such compositions on a large scale for commercial use.

SUMMARY

In an embodiment, a method of producing a fungal entomopathogenic product in liquid culture is disclosed. In an embodiment, a method of producing an entomopathogenic product comprising an entomopathogenic fungal strains selected from the group consisting of *Metarhizium anisopliae* 15013-1 (NRRL 67073), *Metarhizium robertsii* 23013-3 (NRRL 67075), *Metarhizium anisopliae* 3213-1 (NRRL 67074), or any combinations thereof is disclosed. In another embodiment, a method of producing spores in liquid culture is disclosed. In an embodiment, a method of producing microslerotia in liquid culture is disclosed. In another embodiment, a method of producing conidiospores or blastospores in liquid culture is disclosed. In a further embodiment, a method of producing submerged spores in liquid culture is disclosed. In another embodiment, a method of producing vegetative mycelium in liquid culture is disclosed. In a further embodiment, a method comprises obtaining a fungal entomopathogenic product from a liquid medium. In another embodiment, a composition may be the product of a disclosed method of production.

In an embodiment, a method of producing a fungal entomopathogenic product in liquid culture comprising obtaining aerial conidospores of a fungal entomopathogen, inoculating the aerial conidiospores into a liquid medium to generate a fungal entomopahogenic seed culture by fermentation, and inoculating the fungal entomopathogen seed culture into a liquid medium to generate a fungal entomopahogenic product by fermentation, wherein the liquid medium comprises a first carbon source, a second carbon source, and a nitrogen source is disclosed. In a further embodiment, a method comprises obtaining a fungal entomopathogenic product from a liquid medium.

In another embodiment, a composition comprises a fungal entomopathogenic product, wherein the fungal entomopathogenic product has insecticidal activity. A fermentation product may comprise spent media or broth, a fungal entomopathogen, a spore, a mycelium, a microsclerotia, a conidiospore, a blastospore, a submerged spore, a vegetative mycelium, or any other substantially pure component of the fermentation media or lysate.

In another embodiment, a method of producing a fungal entomopathogen in a liquid culture using a carbon source and a nitrogen source is disclosed. In another embodiment, a method of producing a fungal entomopathogen in a liquid culture using a first carbon source, a second carbon source, and a nitrogen source is disclosed. In another embodiment, a method of producing a fungal entomopathogen in a liquid culture using two or more carbon sources and a nitrogen source is disclosed. In an embodiment, a carbon source may include a glucose, a fructose, a galactose, a sorbitol, a sorbose, a sucrose, an arabinose, a maltodextrin, a ribose, or a xylose carbon source and combinations thereof. In another embodiment, a second carbon source comprises a fructose, a galactose, a sorbitol, a sorbose, a sucrose, an arabinose, a maltodextrin, a ribose, or a xylose carbon source and combinations thereof. In a further embodiment, a second carbon source creates a non-optimal or stress condition that changes the physiological state of a fungal entomopathogen. In an embodiment, a first carbon source is in a limiting concentration to facilitate a non-optimal or stress condition of a fungal entomopathogen. In an embodiment, a first carbon source comprises 1, 2, 3, 4, 5, 10, 15, 20, 25, 30, 35, or 40% of the total carbon source amount (weight/volume). In an embodiment, a second carbon source is not in a limiting concentration.

In another embodiment, a method of producing a fungal entomopathogen in a liquid culture using a carbon source and a nitrogen source and controlling a fermentation parameter, wherein controlling the fermentation parameter creates a non-optimal or stress condition that changes a physiological state of a fungal entomopathogen is disclosed. In an embodiment a fermentation parameter may include a pH level, a carbon dioxide evolution rate, a dissolved oxygen percentage, an agitation profile, a sugar feed rate, or any other measured parameter of a fermentation of a fungal entomopathogen that may create a non-optimal or stress condition resulting in a change of a physiological state of a fungal entomopathogen. In a further embodiment, a method of producing a fungal entomopathogen in a liquid culture using a first carbon source, a second carbon source, and a nitrogen source, wherein the second carbon source creates a non-optimal or stress condition that changes a physiological state of a fungal entomopathogen is disclosed.

In an embodiment, a medium for producing a fungal entomopathogenic product comprising a first carbon source, a second carbon source, and a nitrogen source, wherein the second carbon source creates a non-optimal or stress condition of a fungal entomopathogen is disclosed. In an embodiment, a carbon source may include a glucose, a fructose, a galactose, a sorbitol, a sorbose, a sucrose, an arabinose, a maltodextrin, a ribose, or a xylose carbon source and combinations thereof. In another embodiment, a second carbon source comprises a fructose, a galactose, a sorbitol, a sorbose, a sucrose, an arabinose, a maltodextrin, a ribose, or a xylose and combinations thereof. In an embodiment, a first carbon source is in a limiting concentration to facilitate a non-optimal stress condition of a fungal entomopathogen. In an embodiment, a first carbon source comprises 1, 2, 3, 4, 5, 10, 15, 20, 25, 30, 35, or 40% of the total carbon source amount (weight/volume). In an embodiment, a second carbon source is not in a limiting concentration.

DESCRIPTION OF THE DRAWINGS

FIG. 1. Production of *Metarhizium anisopliae* strain 15013-1 fungal propagules during liquid fermentation at shake flask scale; A. Microsclerotia (MS) production after 3, 5, and 7 days of liquid fermentation in soy 10C (25% glucose+75% fructose):1N medium at 300 rpm and 28° C., and B. Submerged spore (SS) production after 3, 5, and 7 days of liquid fermentation in soy 10C (25% glucose+75% fructose): 1N medium at 300 rpm and 28° C.

Figure 2:
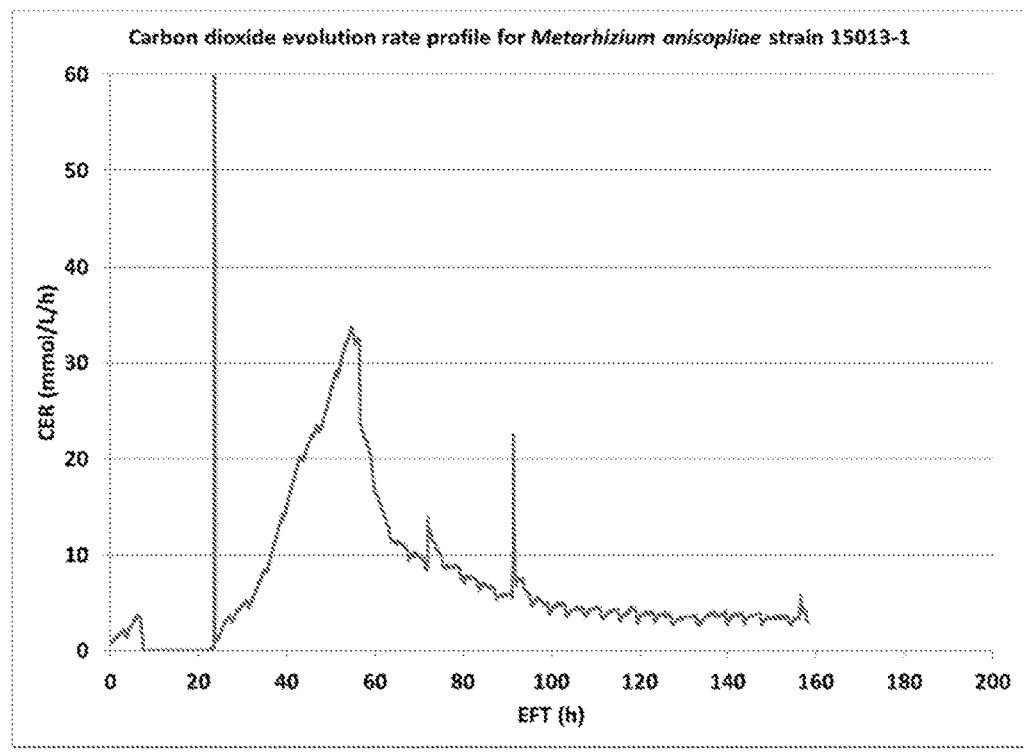
Figure 2:
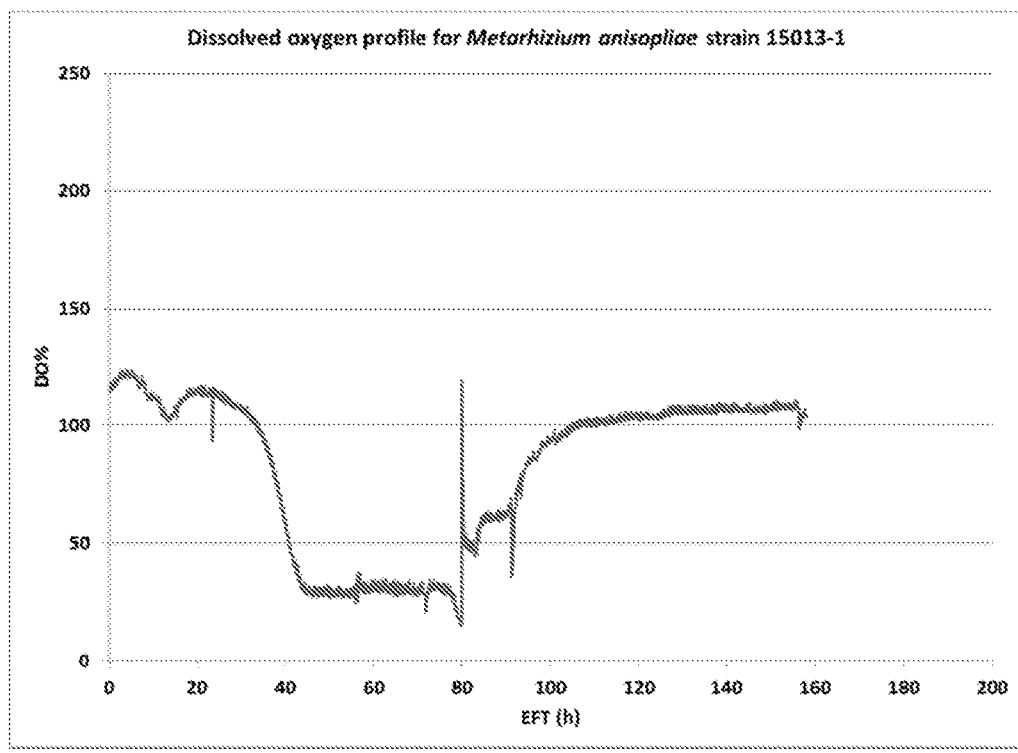
Figure 3:
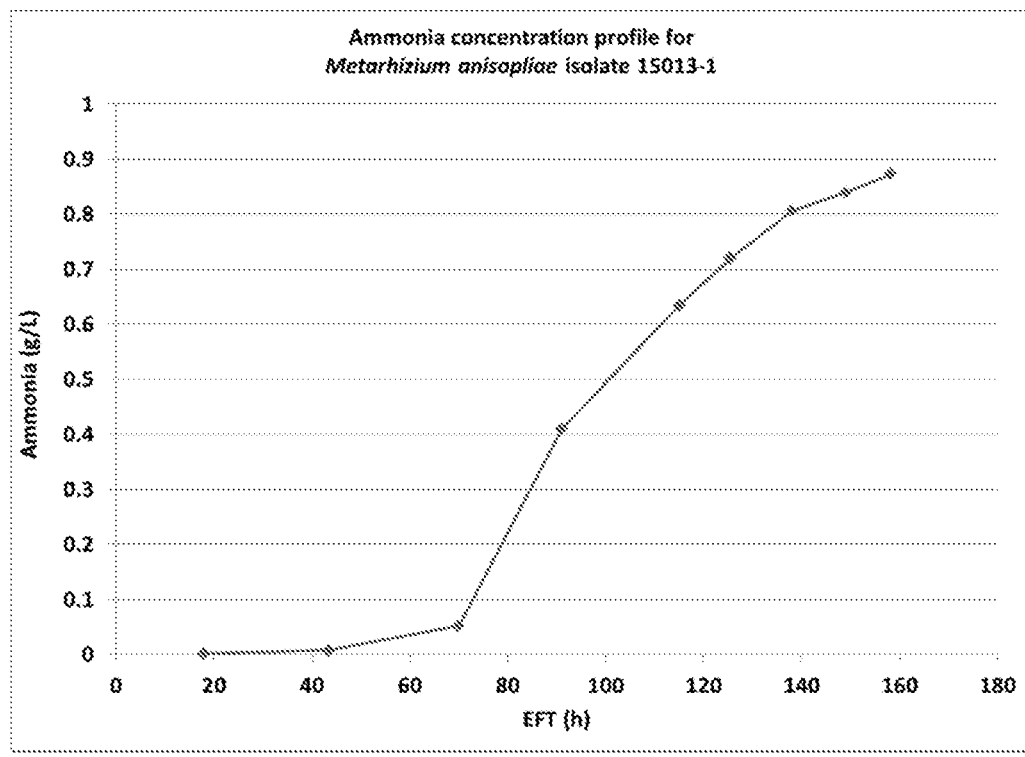
Figure 3:
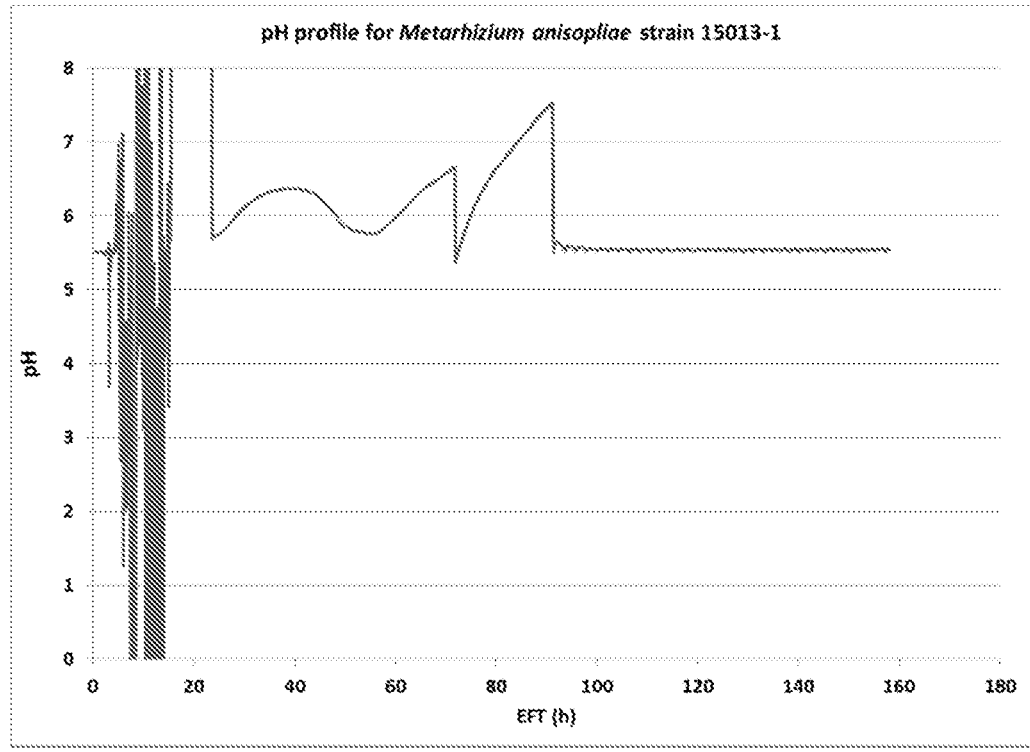
Figure 4:
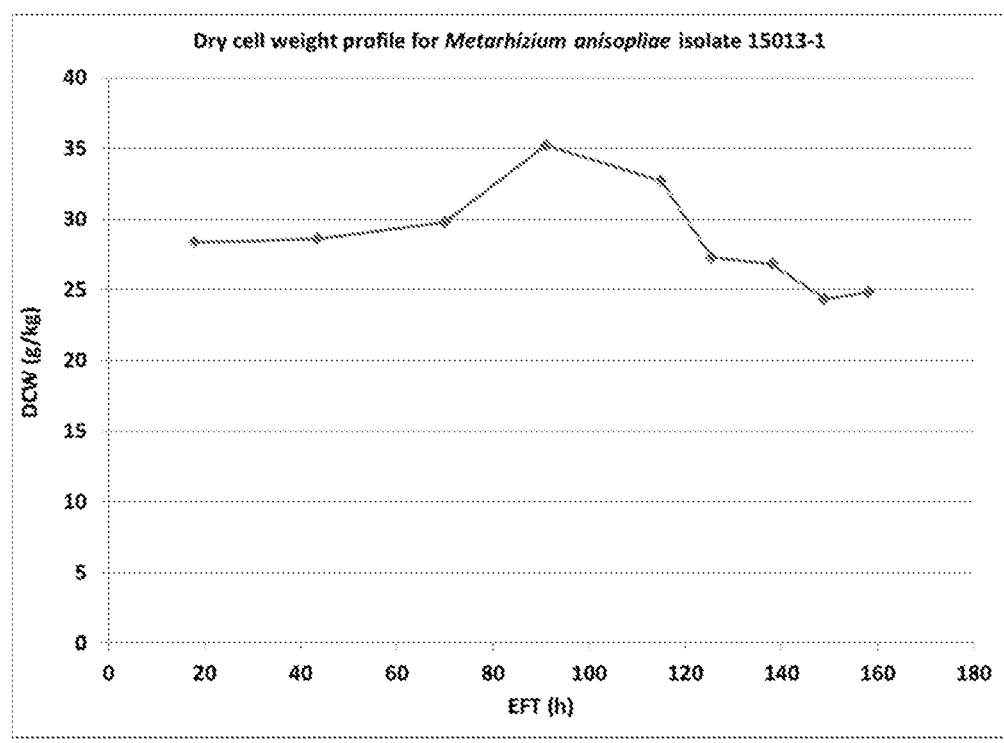
Figure 4:
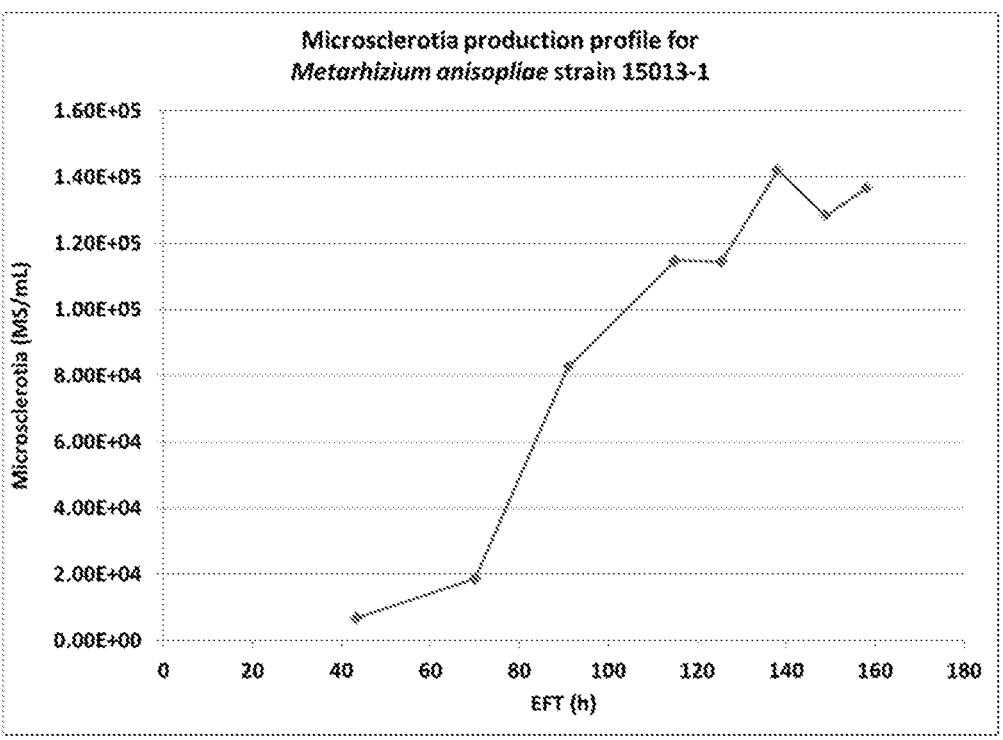
Figure 6:
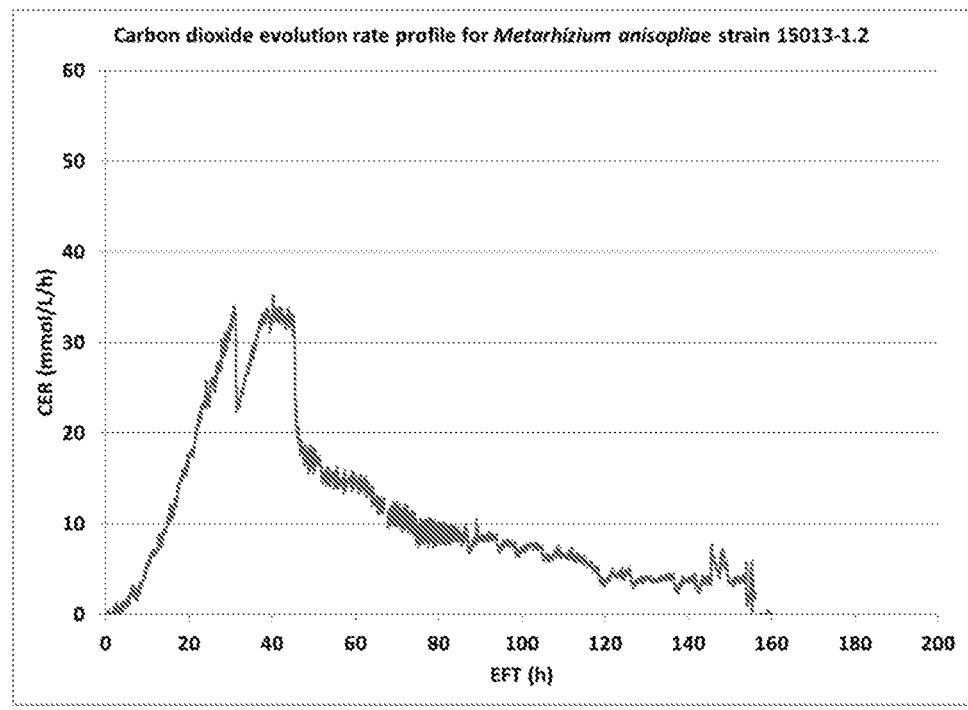
Figure 6:
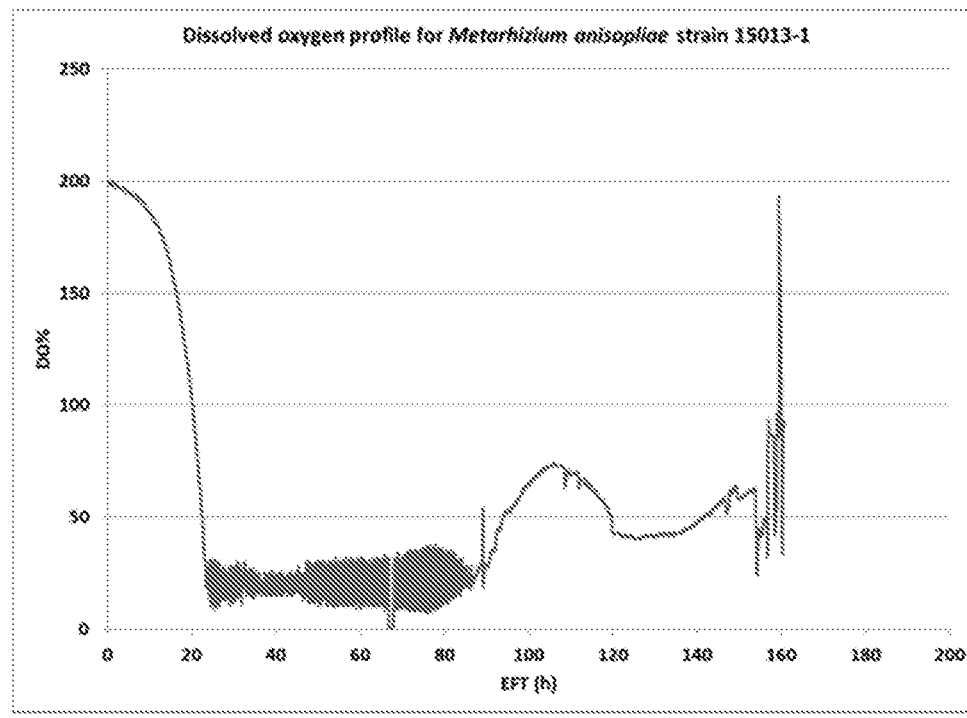
Figure 7:
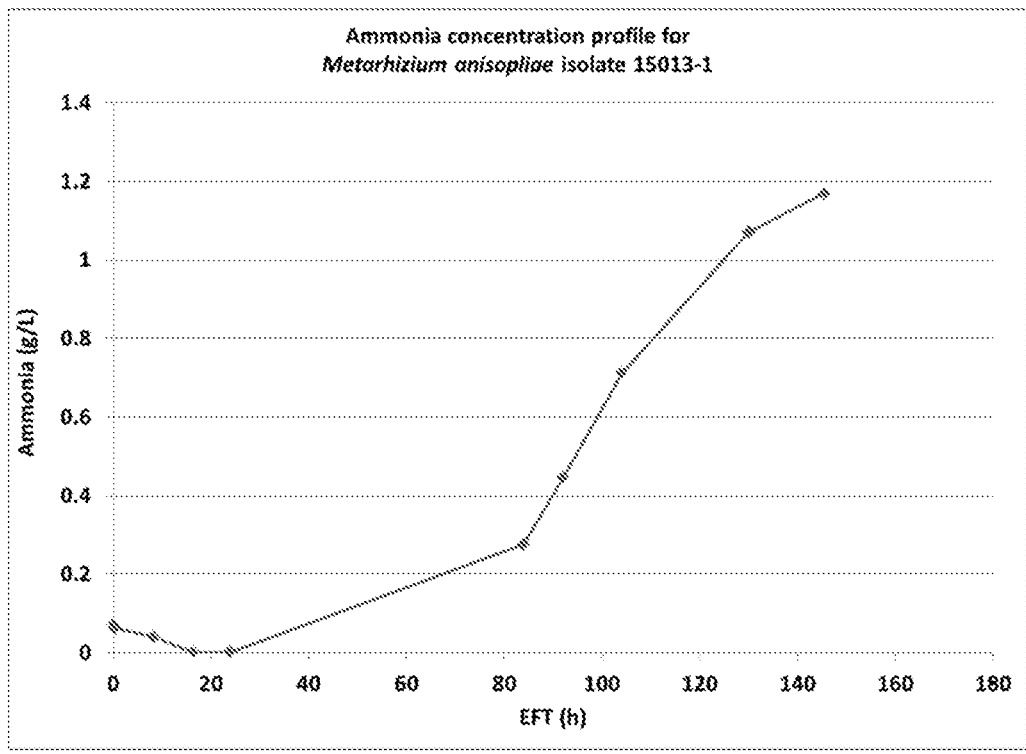
Figure 7:
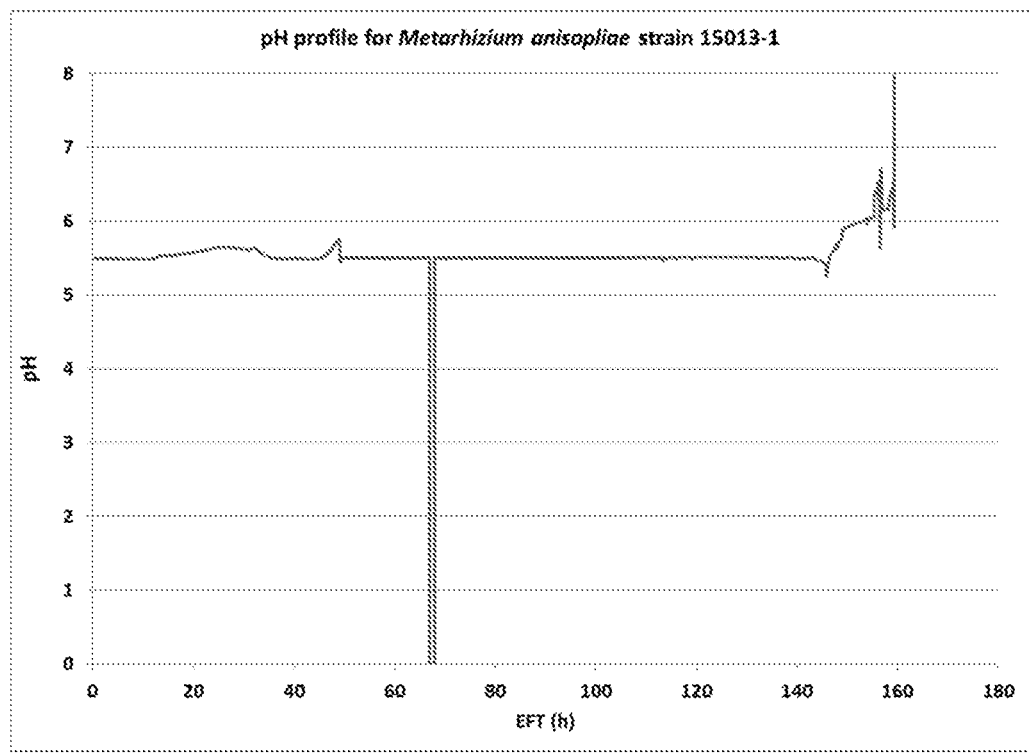
Figure 8:
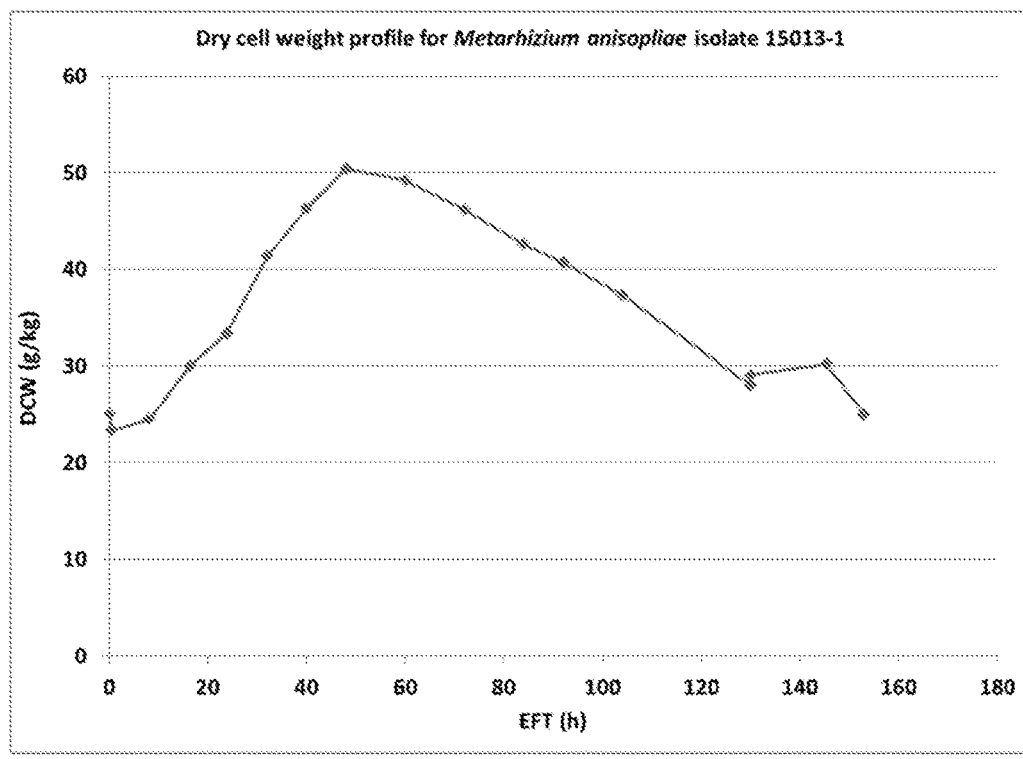
Figure 8:
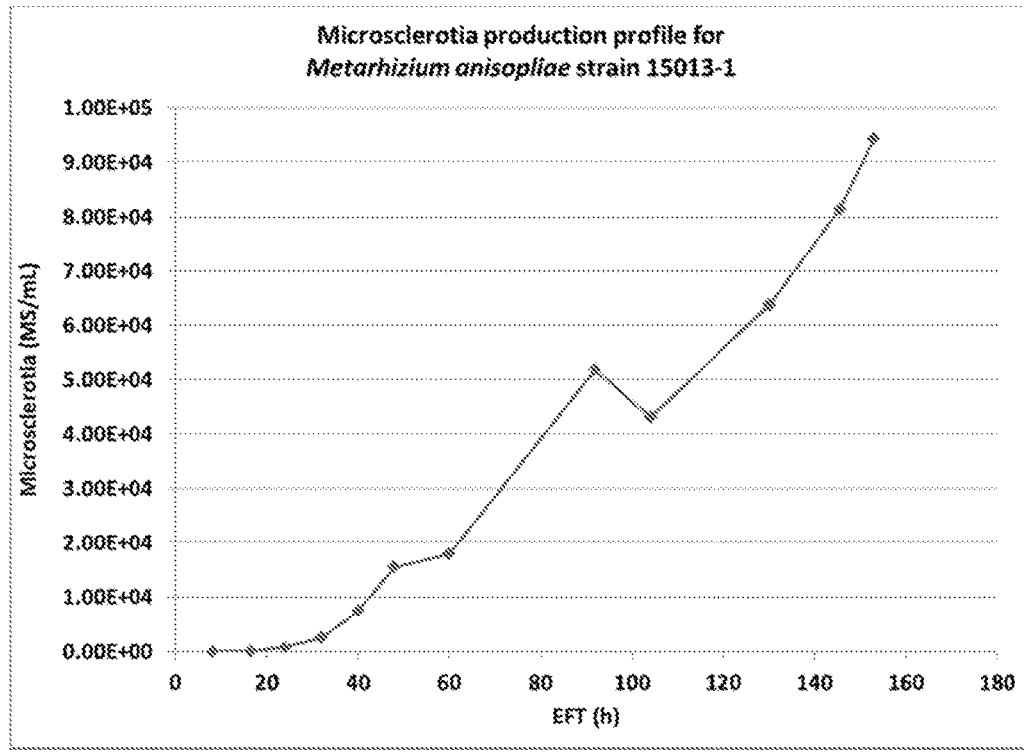
Figure 9:
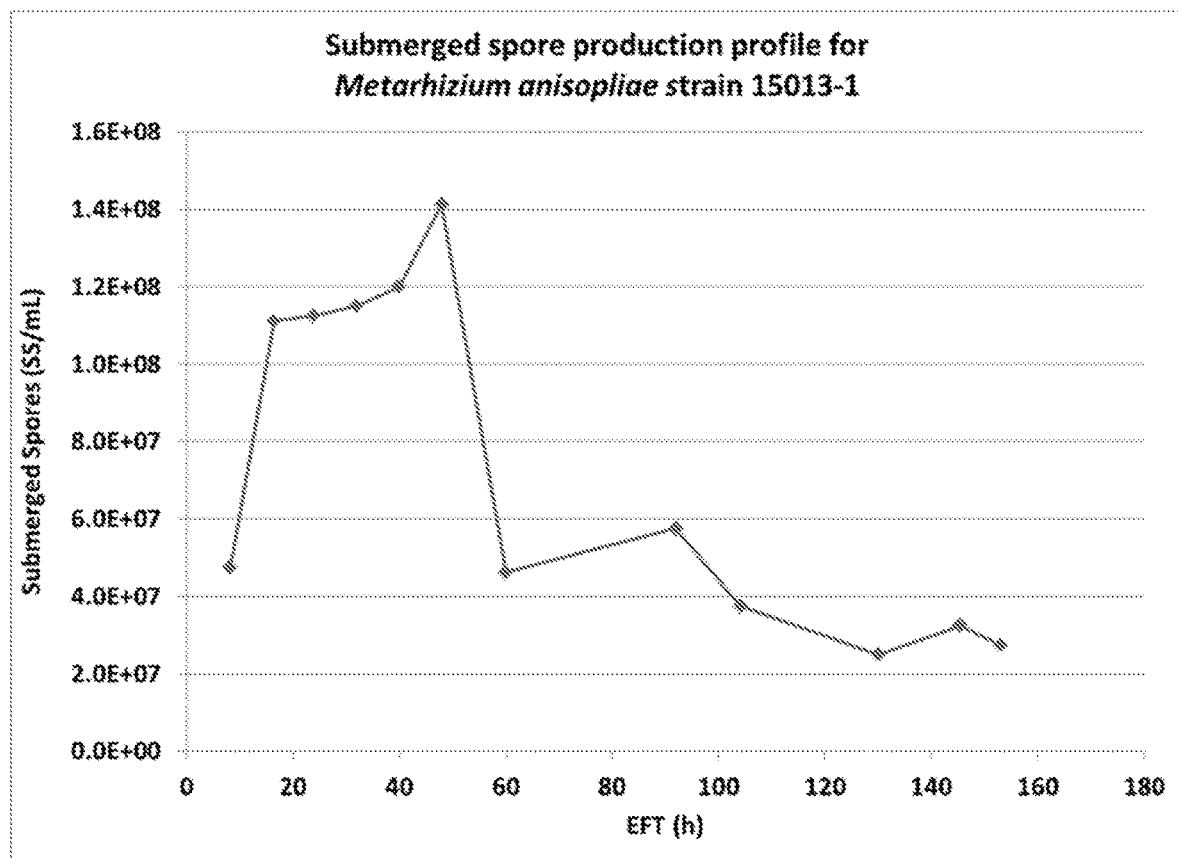
Figure 10:
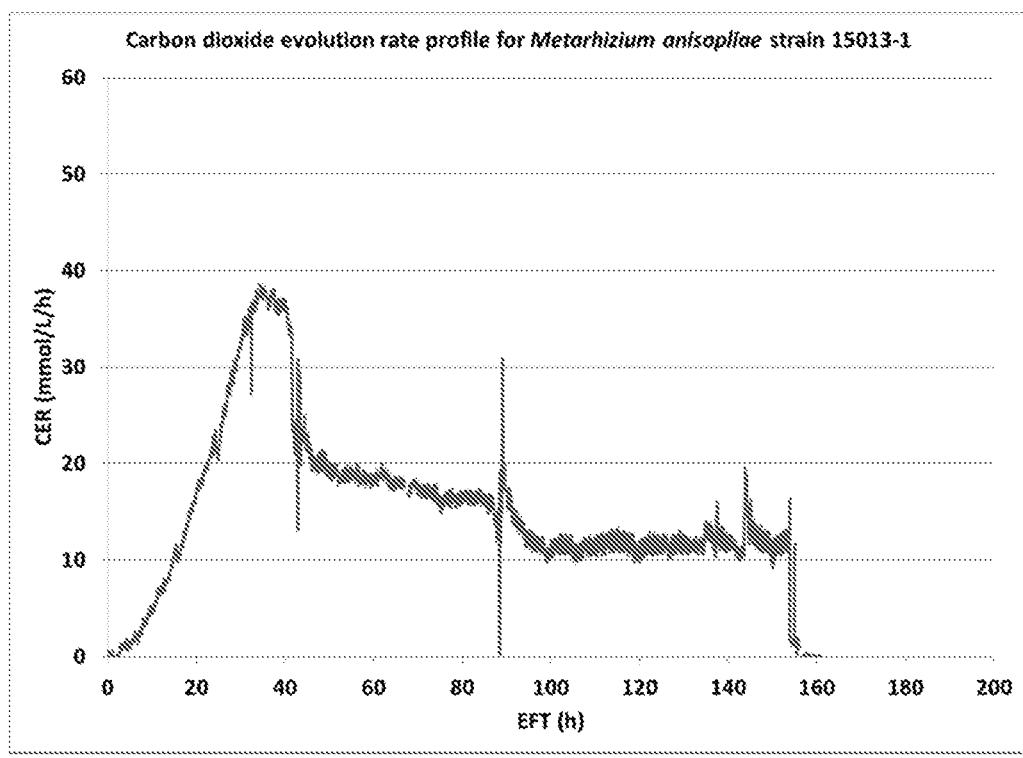
Figure 10:
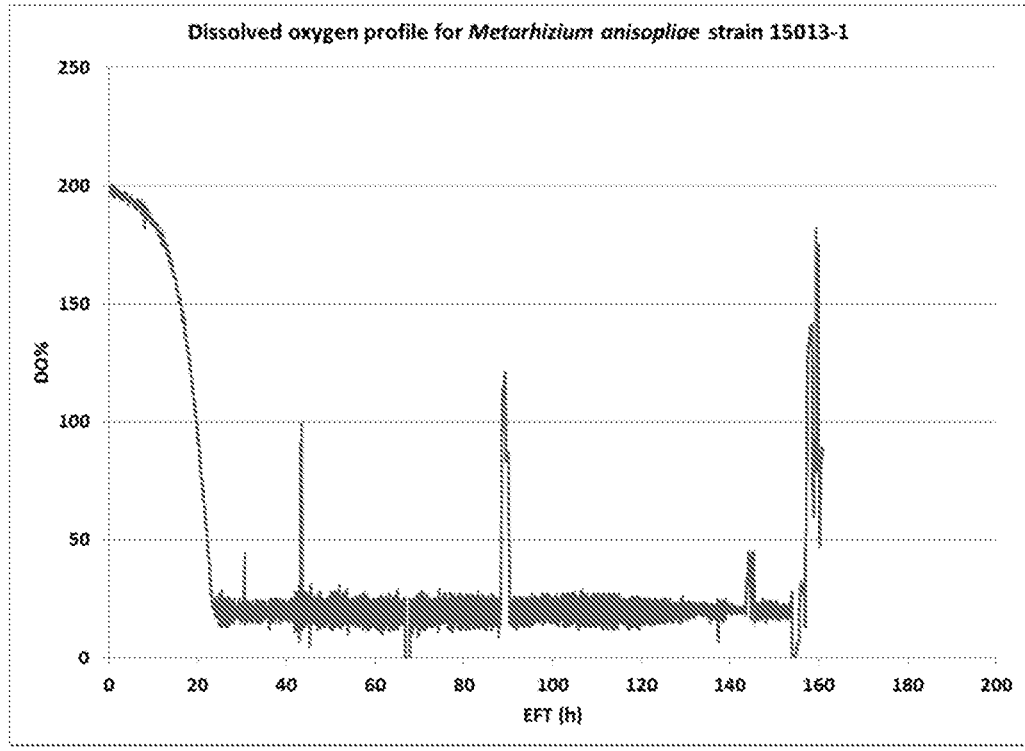
Figure 11:
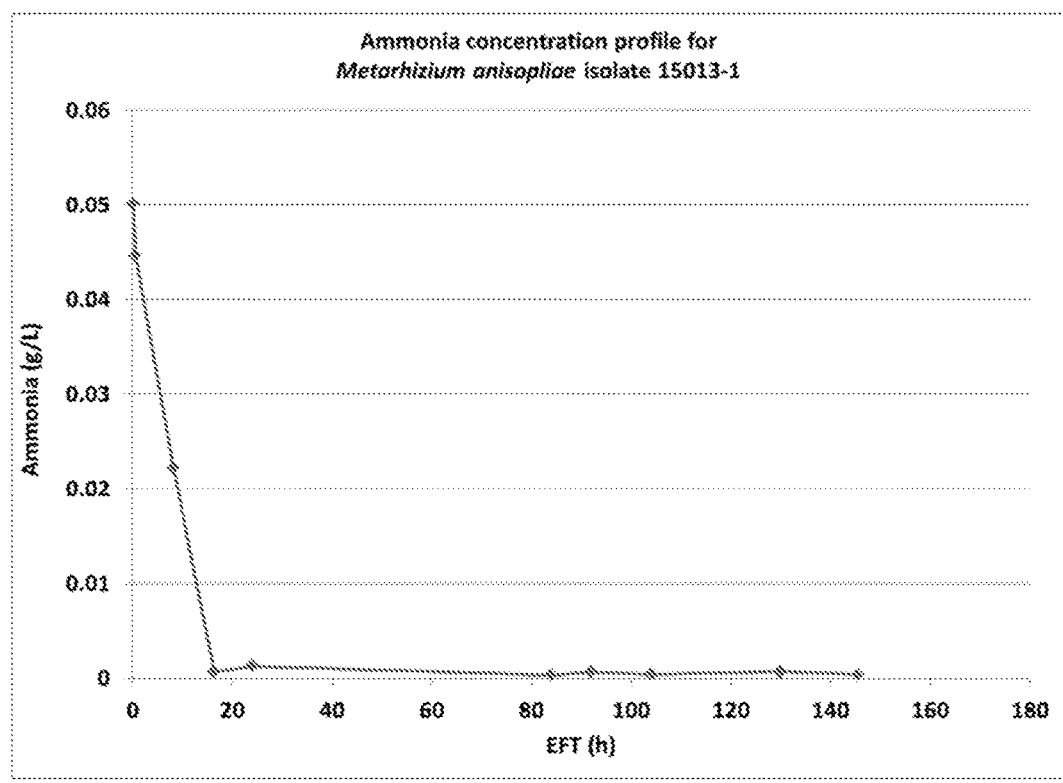
Figure 11:
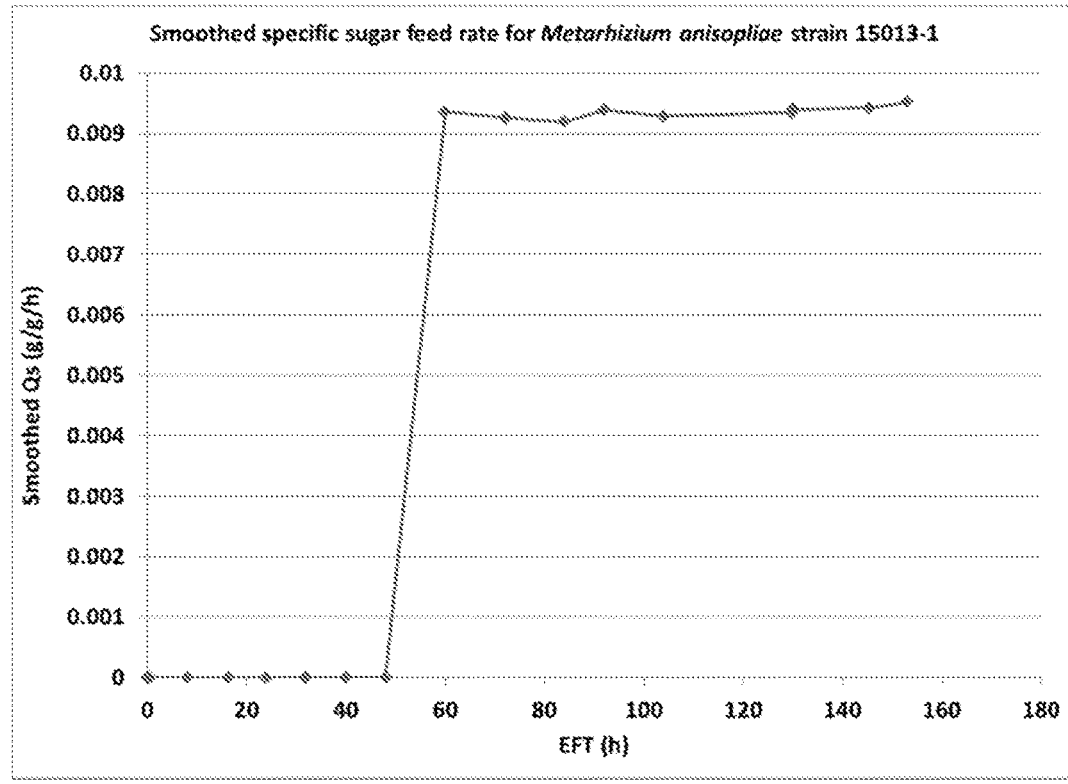
Figure 12:
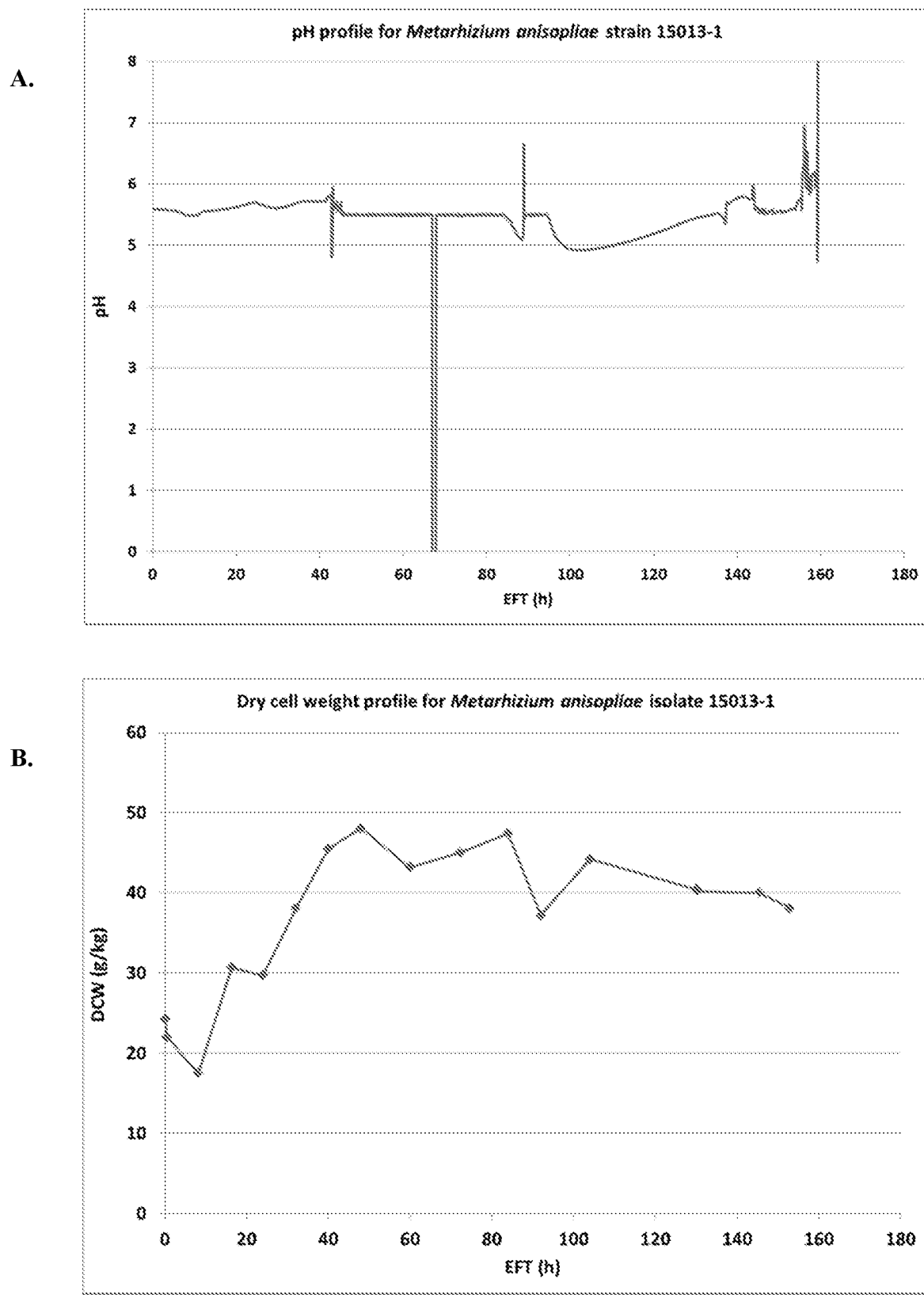
Figure 13:
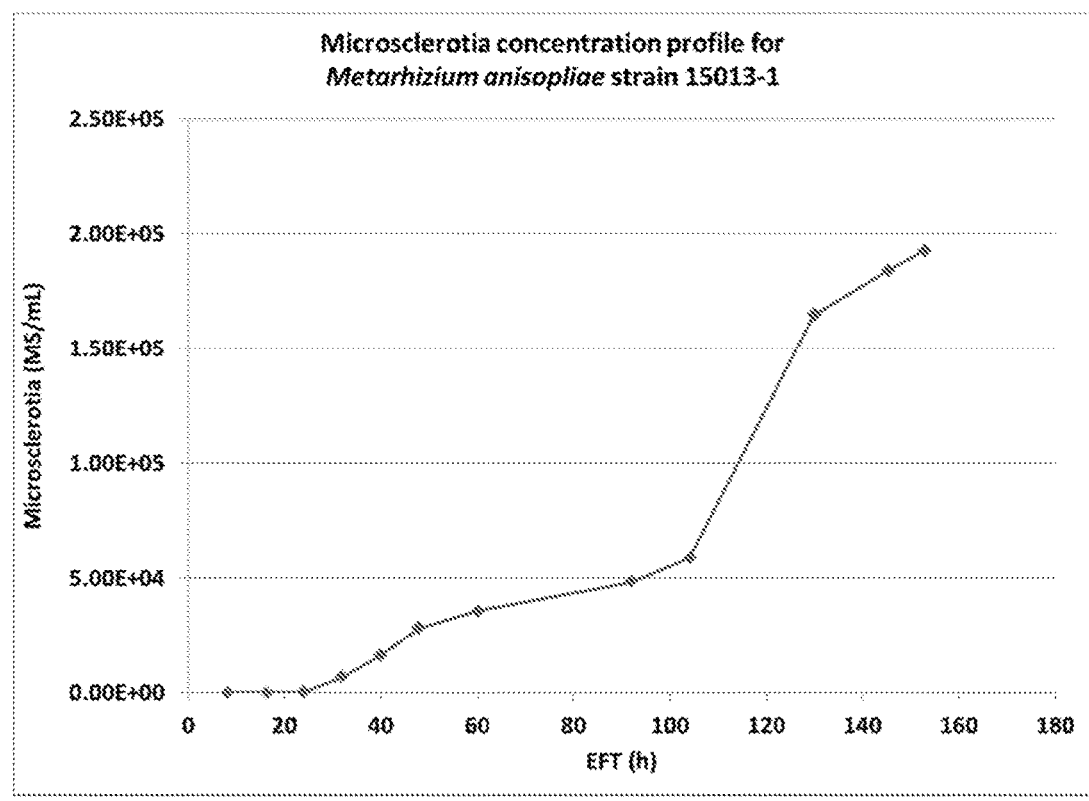
Figure 13:
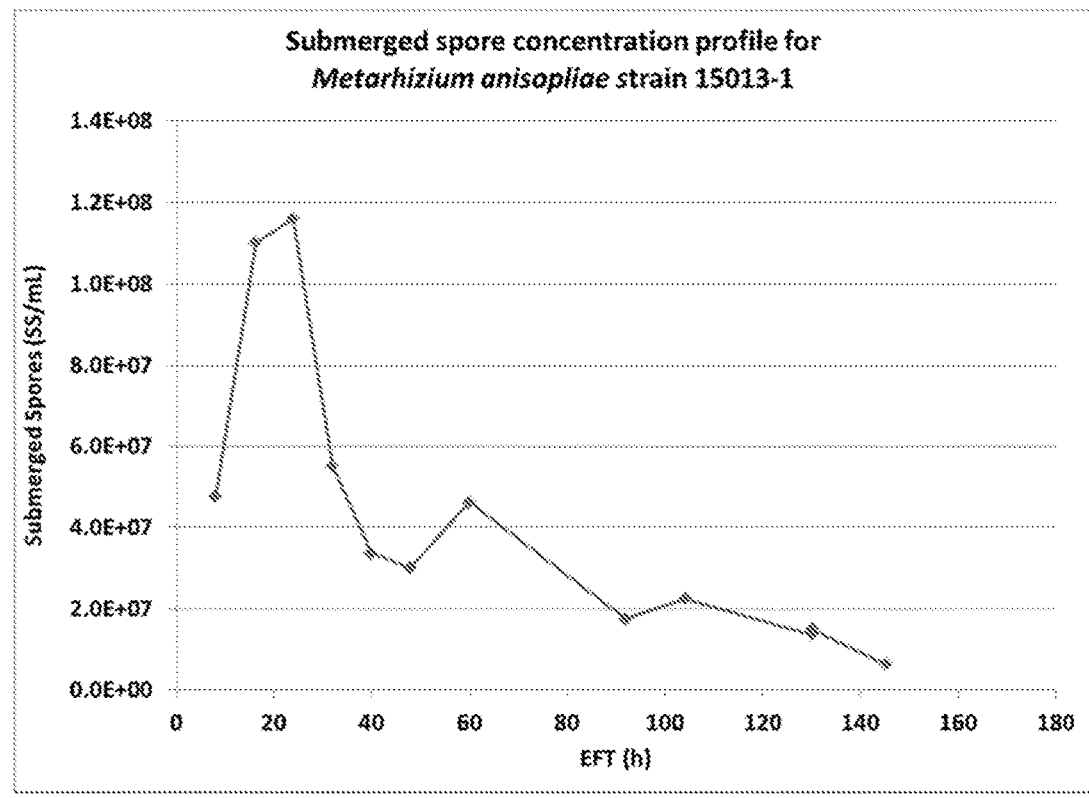
Figure 14:
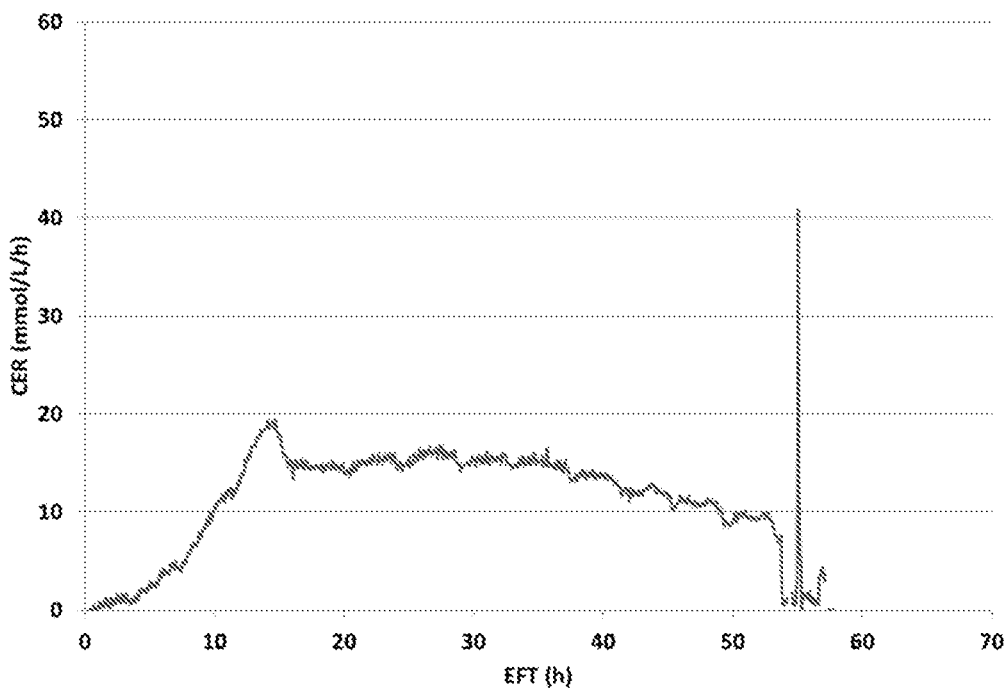
Figure 14:
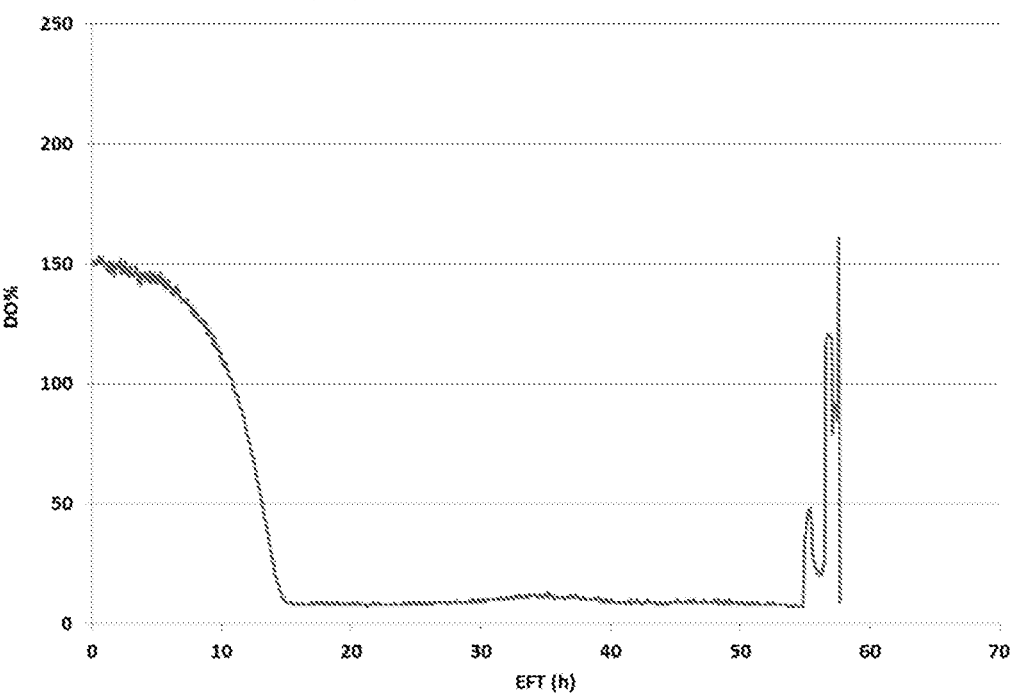
Figure 15:
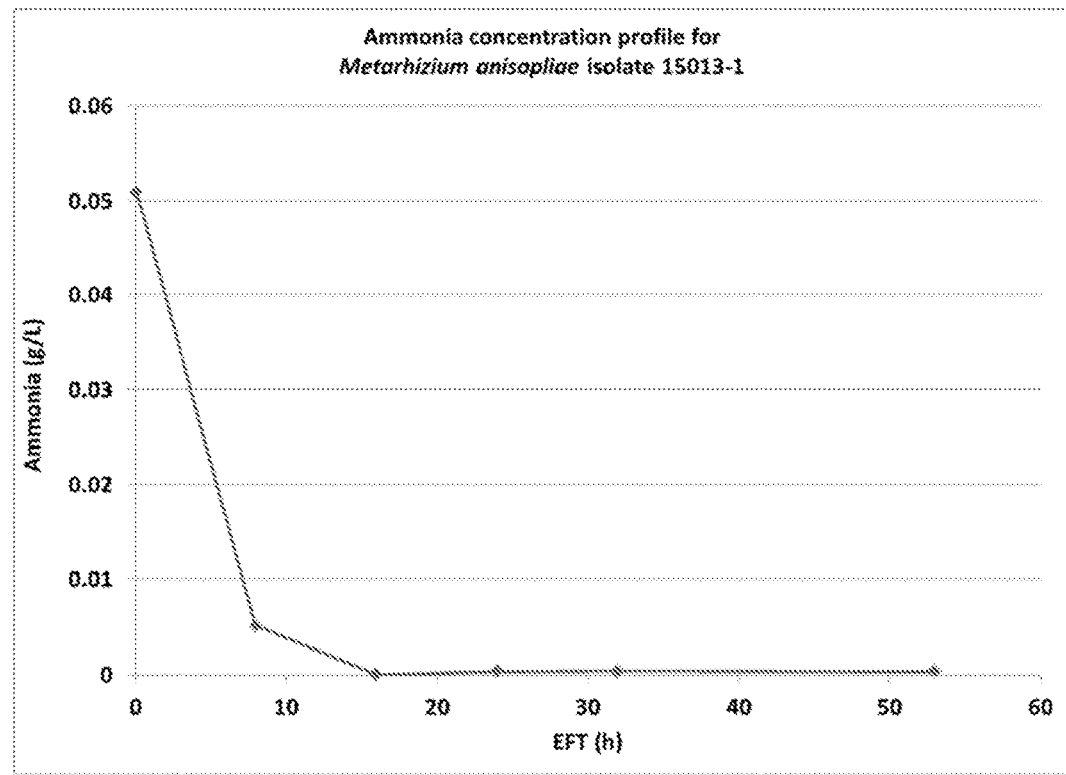
Figure 15:
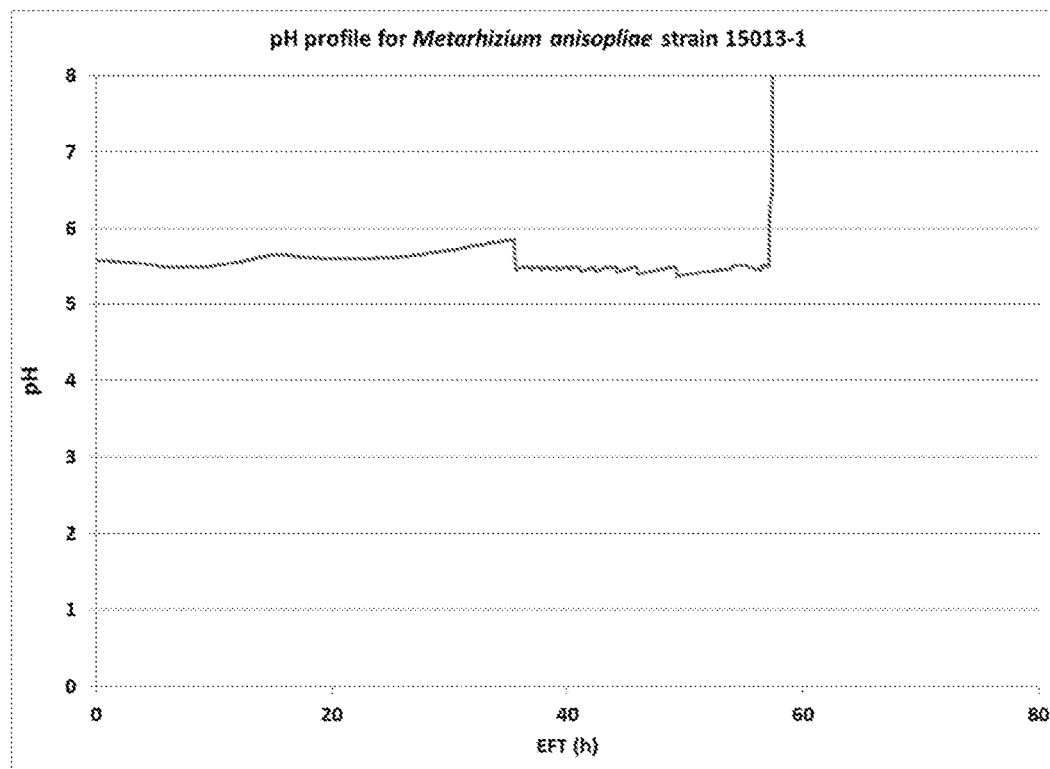
Figure 16:
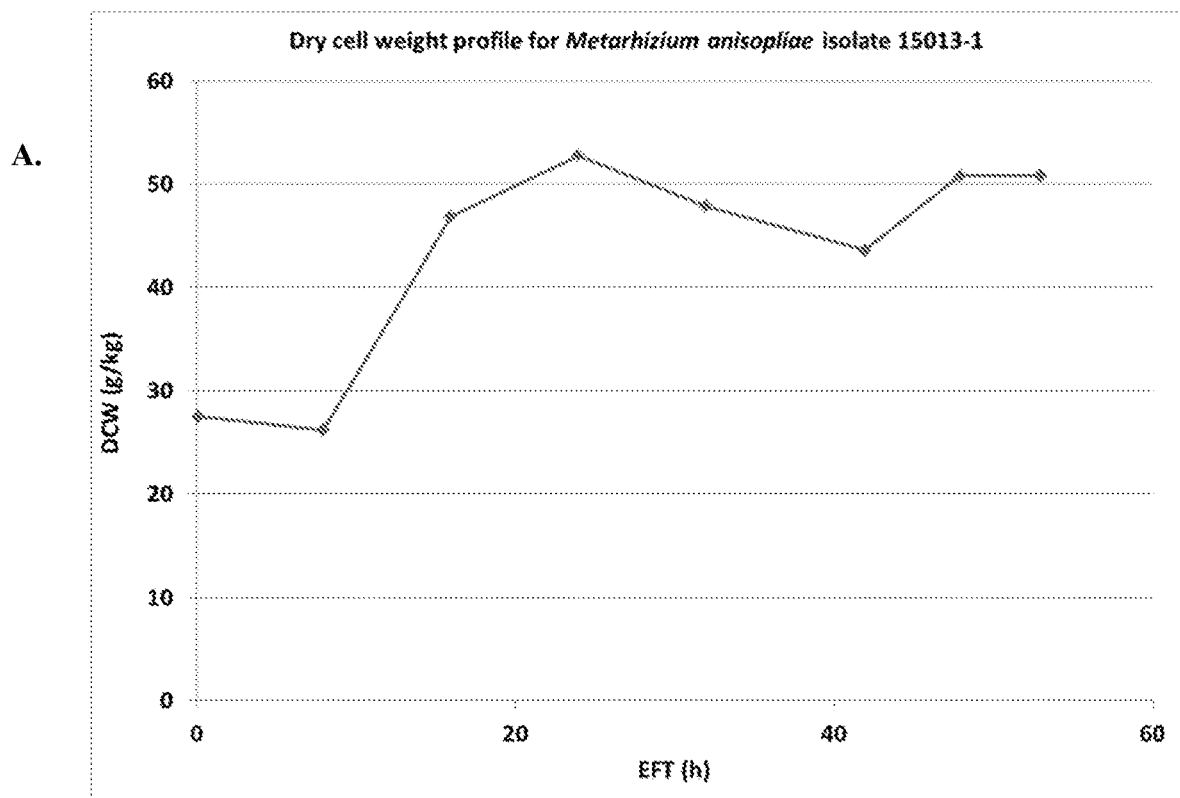
Figure 16:
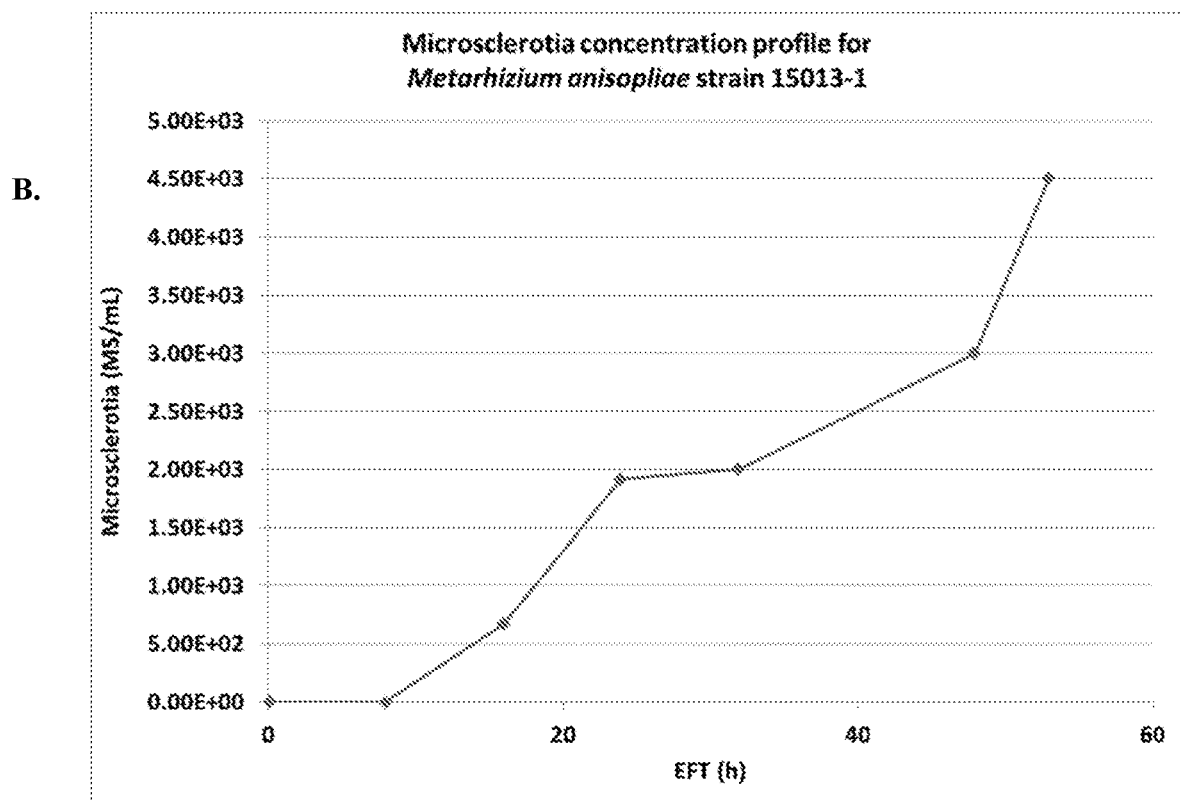

FIG. 2. Fermentation process conditions during production of *Metarhizium anisopliae* strain 15013-1 fungal propagules at 2 L benchtop scale; A. CER profile, and B. DO % profile.

FIG. 3. Fermentation process conditions during production of *Metarhizium anisopliae* strain 15013-1 fungal propagules at 2 L benchtop scale; A. Ammonia concentration profile, and B. pH profile.

FIG. 4. Production of *Metarhizium anisopliae* strain 15013-1 biomass and fungal propagules during fermentation at 2 L benchtop scale; A. Dry Cell Weight (DCW) profile, and B. Microsclerotia (MS) production profile.

Figure 5:
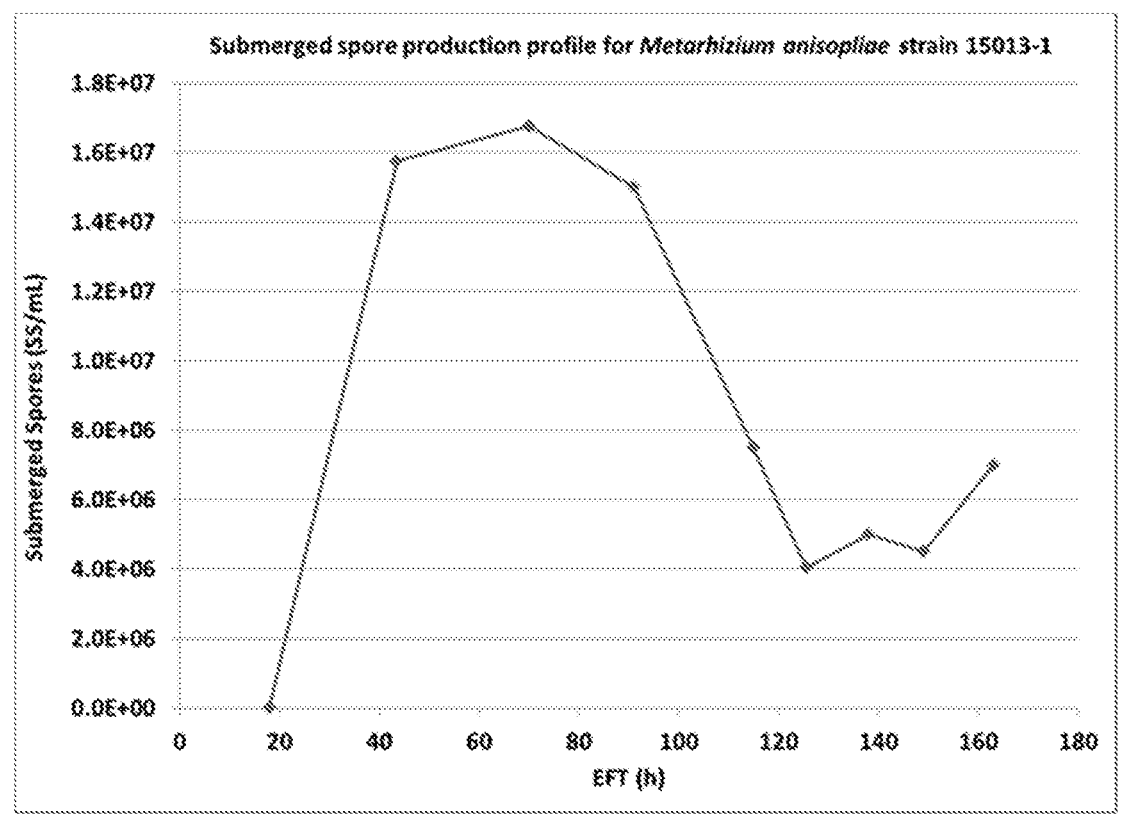

FIG. 5. Submerged spore (SS) production profile of *Metarhizium anisopliae* strain 15013-1 during fermentation at 2 L benchtop scale.

FIG. 6. Fermentation process conditions during production of *Metarhizium anisopliae* strain 15013-1 fungal propagules without feeding; A. CER profile, and B. DO % profile.

FIG. 7. Fermentation process conditions during production of *Metarhizium anisopliae* strain 15013-1 fungal propagules without feeding; A. Ammonia concentration profile, and B. pH profile.

FIG. 8. Production of *Metarhizium anisopliae* strain 15013-1 biomass and fungal propagules during fermentation without feeding; A. Dry Cell Weight (DCW) profile, and B. Microsclerotia (MS) production profile.

FIG. 9. Submerged spore (SS) production profile of *Metarhizium anisopliae* strain 15013-1 during fermentation without feeding.

FIG. 10. Fermentation process conditions during production of *Metarhizium anisopliae* strain 15013-1 fungal propagules with feeding; A. CER profile, and B. DO % profile.

FIG. 11. Fermentation process conditions during production of *Metarhizium anisopliae* strain 15013-1 fungal propagules with feeding; A. Ammonia concentration profile, and B. smoothed specific sugar feed rate profile.

FIG. 12. Fermentation process conditions during production of *Metarhizium anisopliae* strain 15013-1 fungal propagules with feeding at; A. pH profile, and B. Dry Cell Weight (DCW) profile.

FIG. 13. Production of *Metarhizium anisopliae* strain 15013-1 fungal propagules during fermentation with feeding; A. Microsclerotia (MS) production profile, and B. Submerged spore (SS) production profile.

FIG. 14. Fermentation process conditions during production of submerged spore (SS)-enriched *Metarhizium anisopliae* strain 15013-1 fungal propagules; A. CER profile, and B. DO % profile.

FIG. 15. Fermentation process conditions during production of SS-enriched *Metarhizium anisopliae* strain 15013-1 fungal propagules; A. Ammonia concentration profile, and B. pH profile.

FIG. 16. Production of *Metarhizium anisopliae* strain 15013-1 biomass and fungal propagules during fermentation enriched for submerged spore (SS) production; A. Dry Cell Weight (DCW) profile, and B. Microsclerotia (MS) production profile.

FIG. 17. Submerged spore (SS) production profile of *Metarhizium anisopliae* strain 15013-1 during fermentation enriched for SS production.

DETAILED DESCRIPTION

The embodiments of the invention are not limited by the exemplary methods and materials disclosed, and any methods and materials similar or equivalent to those described can be used in the practice or testing of embodiments of this invention. Numeric ranges are inclusive of the numbers defining the range.

The headings provided are not limitations of the various embodiments of this invention, which can be had by reference to the specification.

Definitions of terms appear throughout the specification. It is to be understood the embodiments of the invention are not limited to particular embodiments described, and additional embodiments may vary. It is also to be understood that the terminology used is to describe the embodiments only, and is not intended to be limiting, since the scope of the embodiments of the invention will be limited only by the appended claims and equivalents thereof.

The article "a" and "an" are used to refer to one or more than one (i.e., to at least one) of the grammatical object of the article. For example, "an element" means one or more element.

As used herein, the terms "liquid fermentation" and "fermentation" refer to growth of the fungal entomopathogen in liquid medium to produce various cellular structures. As used herein, the term "seed culture" refers to a liquid culture or solid state fermentation product used to build up the biomass required for starting a production culture. As used herein, the term "biomass" includes all the structures that can be formed by the fungal enotmopathogen in liquid medium. As used herein, the term "dry cell weight" (DCW) refers to grams of dry weight per kilogram of broth, and will be used as a measure of biomass accumulation. As used herein, the term CER refers to the rate of carbon dioxide produced in the bioreactor defined as mmol $CO_2$/L of broth/h (Buckland et al., 1985 *BioTechnology*). As used herein, the term fermentation dissolved oxygen (DO %) is expressed in % of air saturation.

As used herein, the term a "carbon source" refers to any complex or simple carbohydrate capable of sustaining survival, growth, or production of particular fungal structures of a fungal entomopathogen. In an embodiment, a carbon source may be provided in a fermentation through a feed. In a further embodiment, the carbon source provided in a feed comprises glucose or fructose. As used herein, a "limiting concentration" of a carbon source means a main carbon source, glucose for example, is depleted and the organism must switch to using a second carbon source for survival, growth, or production of particular fungal structures. As used herein, a "nitrogen source" refers to a complex nitrogen source that may comprise carbon, but is not a carbon source capable of sustaining survival, growth, or production of particular fungal structures of a fungal entomopathogen. In an embodiment, a nitrogen source comprises soy, defatted meal, protein concentrate, protein isolate, a hydrolysate, yeast or other extract, molasses or a combination thereof.

As used herein, the term "fermentation product" refers to a composition comprising a vegetative mycelium, a spore, a conidiospore, a blastospore, an aerial conidiospore, a submerged conidiospore, a submerged blastospore, and/or a microsclerotia of a fungal entomopathogen that is produced through a fermentation process. In an embodiment, a fermentation product comprises a *Metarhizium* fungal entomopathogen. In another embodiment, a fermentation product comprises an entomopathogenic fungal strain selected from the group consisting of *Metarhizium anisopliae* 15013-1, *Metarhizium robertsii* 23013-3, *Metarhizium anisopliae* 3213-1. A fermentation product may be obtained from a fermentation process using vacuum drying. In an embodiment, a fermentation product is capable of surviving or being dessicant resistant for downstream applications or formulations.

In an embodiment of the invention, a method of producing a fungal entomopathogen product in a liquid fermentation is disclosed. In an embodiment, a method consists of first generating aerial conidiospores of a fungal entomopathogen on an agar media, and then inoculating the aerial conidiospores into a liquid medium to generate a fungal entomopathogen product. In another embodiment, a method consists of first generating aerial conidiospores of a fungal entomopathogen on a solid substrate, including, but not limited to, an agar media or other solid media of appropriate composition, followed by inoculating the aerial conidiospores into a liquid medium to generate a fungal entomopathogen seed culture, followed by inoculating the fungal entomopathogen seed culture into a liquid medium to generate a fungal entomopathogen product. In another embodiment, a first fungal entomopathogen seed culture may be used to generate a second fungal entomopathogen seed culture, wherein the second seed culture is used to inoculate into a liquid medium to generate a fungal entomopathogen product. A liquid medium used to produce a fungal entomopathogen product may contain minerals, vitamins, a carbon source and a complex nitrogen source. In another embodiment, a nitrogen source is a complex source that comprises carbon, but is not a carbon source. In an embodiment, a method to produce a fungal entomopathogen product comprising a spore, a vegetative mycelium, a submerged spore, and/or a microsclerotia is disclosed. In an embodiment, a composition comprises a fermentation product of a fungal entomopathogen from a liquid fermentation. A fermentation product may be vacuum dried for use to control plant pathogens, pests, or insects.

In an embodiment of the invention, a method of producing a fungal entomopathogen product in a liquid fermentation, wherein the liquid fermentation comprises a liquid medium comprising minerals, vitamins, a carbon source, and a nitrogen source is disclosed. In an embodiment, a method of producing a fungal entomopathogen in a liquid culture using a carbon source and a nitrogen source is disclosed. In another embodiment, t a method of producing a fungal entomopathogen in a liquid culture using two carbon sources and a nitrogen source is disclosed. In another embodiment, a method of producing a fungal entomopathogen in a liquid culture using two or more carbon sources and a nitrogen source is disclosed. In an embodiment, a carbon source is glucose. In another embodiment, a carbon source comprises a fructose, a galactose, a sorbitol, a sorbose, a sucrose, an arabinose, a maltodextrin, a ribose, or a xylose molecule and combinations thereof. In another embodiment, a first carbon source is in a limiting concentration. In a further embodiment, a second carbon source creates a non-optimal or stress condition that changes a physiological state of a fungal entomopathogen. In another embodiment, a method of producing a fungal entomopathogen in a liquid culture using a carbon source, a first nitrogen source, and a second nitrogen source, wherein the first nitrogen source is in a limiting concentration is disclosed.

In another embodiment, a method of producing a fungal entomopathogen in a liquid culture using a carbon source and a nitrogen source and controlling a fermentation parameter, wherein controlling the fermentation parameter creates a non-optimal or stress condition that changes a physiological state of a fungal entomopathogen is disclosed. In an embodiment a fermentation parameter may include a pH level, a carbon dioxide evolution rate, a dissolved oxygen percentage, an agitation profile, a sugar feed rate, or any other measured parameter of a fermentation of a fungal entomopathogen that may create a non-optimal or stress condition resulting in a change of a physiological state of a fungal entomopathogen. Physiological changes (switch to asexual cycle) may occur as a result of imposing stress or non-optimal conditions on a fungal emtomopathogen. (See Steyaert et al. (2010), *Microbiol*. and Gao et al. (2007) *Mycol. Res*). In another embodiment, a method of producing a fungal entomopathogen in a liquid culture using at least two carbon sources and a nitrogen source and controlling a fermentation parameter, wherein controlling the fermentation parameter creates a non-optimal or stress condition that results in a change of a physiological state of a fungal entomopathogen is disclosed. In an embodiment, obtaining aerial conidospores of a fungal entomopathogen comprises first generating aerial conidiospores of the fungal entomopathogen on an agar media or a solid state media (Dorta and Arcas (1998), *Enzyme Microb. Technol*.).

An embodiment of the invention relates to a method for producing a fungal entomopathogen, wherein the fungal entomopathogen comprises or consists of or consists essentially of an entomopathogenic fungal strain selected from the group consisting of: *Metarhizium anisopliae* 15013-1, *Metarhizium robertsii* 23013-3, and *Metarhizium anisopliae* 3213-1. In another embodiment, a method comprises, consists of, or consists essentially of at least two or more entomopathogenic fungal strains selected from the group consisting of: *Metarhizium anisopliae* 15013-1, *Metarhizium robertsii* 23013-3, *Metarhizium anisopliae* 3213-1.

In an embodiment, a method for producing a fungal entomopathogenic product comprises generation of aerial conidiospores (AC) used as an inoculum for liquid cultures or liquid fermentations. Such methods include, but are not limited to, generation of ACs by inoculating a fungal entomopathogen strain on large PDA or VM plates and incubating at 28° C. for about 2 to 3 weeks; flooding the plates with a solution of 0.05% Tween 80; and suspending ACs in the solution by gently scraping the surface of the plate culture. In an embodiment, an AC suspension may be filtered, and the ACs pooled to a high concentration. In a further embodiment, an AC concentration may be determined using a hemocytometer, the ACs centrifuged, and the AC pellet re-suspended using a solution of 15% glycerol in 0.05% Tween 80. In another embodiment, aerial conidiospores may also be obtained by solid state fermentation (Dorta and Arcas (1998), *Enzyme Microb. Technol*.).

In an embodiment, producing a fungal entomopathogen product in a liquid culture may comprise media volumes of 50 mL at shake flask fermentation scale, 1 L at 2 L benchtop fermentation scale, and 10 L at bioreactor fermentation scale, or up to 600,000 L fermentation scale. Media for seed or production cultures may comprise components as shown in Tables 1, 2 and 3. At shake flask scale media may be inoculated directly with aerial conidiospores (AC) at a final concentration of about $5\times10^6$ AC/mL. At benchtop or bioreactor scale media may be inoculated using a seed culture of about 40 mL or 400 mL of seed culture, respectively. A seed culture may be produced to build up biomass for a production culture. Seed cultures may be generated by further incubating a culture from about 1 to 7 days at about 28° C., and agitating from about 100 to 300 rpm. Upon addition of an inoculum, production cultures may be incubated from about 4 to 7 days at about 16° C. to 32° C. in an orbital shaker at about 300 rpm at shake flask scale; about 500 to 1200 rpm agitation at benchtop scale; or with agitation speeds equivalent to the benchtop impeller tip speed at bioreactor scale. In certain embodiments, water may be added to reduce the viscosity of a broth during fermentation. Pressure in a fermentation tank may be set at about 0.5 to 1 barg. In certain embodiments, a 50% (w/w) fructose solution may be fed after an initial glucose and fructose solution is exhausted. In certain embodiments, a seed or a production culture may have no pH control, one-sided (base addition only) pH control, or two-sided (base and acid addition) pH control. During a fermentation and/or at the end of a fermentation a variety of parameters may be recorded, such as, but not limited to, microsclerotia (MS) production, submerged spore (SS) production, biomass build-up expressed through grams of dry cell weight per kilogram of broth (DCW), carbon evolution rate (CER), oxygen uptake rate (OUR), dissolved oxygen (DO), ammonia concentration, pH, feed rate, carbon source content, and agitation.

TABLE 1

Vitamins present in all media.

| Vitamins | Final concentration [mg/L] |
|---|---|
| Thiamine•HCl (Vit. B1) | 0.5 |
| Riboflavin (Vit. B2) | 0.5 |
| Calcium Pantonthenate (Vit. B5) | 0.5 |
| Nicotinic Acid (Vit. B3) | 0.5 |
| Pyridoxamine | 0.5 |
| Thioctic Acid (Lipoic Acid) | 0.5 |
| Folic Acid (Vit. B9) | 0.05 |
| D-Biotin (Vit. B7) | 0.05 |
| Cobalamin (Vit. B12) | 0.05 |

TABLE 2

Basal salts present in all media.

| Basal salts | Final concentration [amount/L] |
|---|---|
| $KH_2PO_4$ | 4 g |
| $CaCl_2 \cdot 2H_2O$ | 0.8 g |
| $MgSO_4 \cdot 7H_2O$ | 0.6 g |
| 0.1M $CoCl_2$ | 1.555 mL |
| 10 g/L $MnSO_4 \cdot H_2O$ | 1.6 mL |
| 10 g/L $ZnSO_4 \cdot 7H_2O$ | 1.4 mL |

TABLE 3

Carbon and nitrogen sources in different liquid media.

| source concentrations in different media | Soy 10C:1N | Soy 10C:1N 25% Glu75% Fru | Soy 10C:1N 25% Glu75% Gal | Soy 10C:1N 25% Glu75% Sorbitol | Soy 10C:1N 25% Glu75% Sorbose | Soy 10C:1N 25% Glu75% Suc |
|---|---|---|---|---|---|---|
| Soy flour | 45 g | 45 g | 45 g | 45 g | 45 g | 45 g |
| D-Glucose | 49.5 g | 12.375 g | 12.375 g | 12.375 g | 12.375 g | 12.375 g |
| D-Fructose | | 37.125 g | | | | |
| D-Galactose | | | 37.125 g | | | |
| D-Sorbitol | | | | 37.125 g | | |
| L-Sorbose | | | | | 37.125 g | |
| Sucrose | | | | | | 37.125 g |
| L-Arabinose | | | | | | |
| Maltodextrin | | | | | | |
| D-ribose | | | | | | |
| D-xylose | | | | | | |

| source concentrations in different media | Soy 10C:1N 25% Glu75% Ara | Soy 10C:1N 25% Glu75% Mal | Soy 10C:1N 25% Glu75% Rib | Soy 10C:1N 25% Glu75% Xyl |
|---|---|---|---|---|
| Soy flour | 45 g | 45 g | 45 g | 45 g |
| D-Glucose | 12.375 g | 12.375 g | 12.375 g | 12.375 g |
| D-Fructose | | | | |
| D-Galactose | | | | |
| D-Sorbitol | | | | |
| L-Sorbose | | | | |
| Sucrose | | | | |
| L-Arabinose | 37.125 g | | | |
| Maltodextrin | | 37.125 g | | |
| D-ribose | | | 37.125 g | |
| D-xylose | | | | 37.125 g |

*In some cases, soy flour was substituted with other sources of nitrogen, such as, but not limited to cottonseed flour, yeast extract or Casamino acids; in some cases the ratio of carbon (C) to nitrogen (N) was 30:1, or 50:1.

In certain embodiments, recovering and formulating a fungal entomopathogen (*Metarhizium* spp.) product from a liquid culture comprises cooling and harvesting a fermentation broth. A fermentor may be rinsed with about 1× to 2× the volume of a fermentation broth, and the diluted broth pooled with the neat broth. A diluted entomopathogenic fungal material in a fermentation broth may be treated with DE Admix. A treated fermentation broth may be filtered through a Büchner filter. A filter cake may be processed immediately, or stored in a cold room until processing. A wet filter cake may be broken up and dried in a vacuum drier for about 48 h to 5 days. A dried filter cake may be ground to create a final entomopathogenic fungal dried powder product.

As used herein, "administer" refers to the action of introducing a strain and/or a composition to an environment for pathogen, pest, or insect inhibition or to improve plant performance.

As used herein, the term "agrochemically active compounds" refers to any substance that is or may be customarily used for treating plants including but not limited to fungicides, bactericides, insecticides, acaricides, nematicides, molluscicides, safeners, plant growth regulators, and plant nutrients, as well as, microorganisms.

As used herein, a composition may be a liquid, a heterogeneous mixture, a homogeneous mixture, a powder, a solution, a dispersion or any combination thereof.

As used herein, "effective amount" refers to a quantity of an entomopathogenic fungal strain or a composition sufficient to inhibit growth of a pathogenic microorganism or to impede the rate of growth. In another embodiment, the term "effective amount" refers to a quantity of an entomopathogenic fungal strain or a composition sufficient to improve plant performance. In another embodiment, the term "effective amount" refers to a quantity of an entomopathogenic fungal strain or a composition sufficient to control, kill, inhibit, and reduce the number, emergence, or growth of a pathogen, pest, or insect. In another embodiment, the term "effective amount" refers to a quantity of an entomopathogenic fungal strain or a composition sufficient to prevent damage from a pathogen, pest, or insect. One skilled in the art will recognize that an effective amount of an entomopathogenic fungal strain or a composition may not reduce the numbers of pathogens, pests or insects, but is effective in decreasing damage to plants as a result of a pathogen, pest or insect. For example, a pesticidally effective amount may reduce pathogen, pest or insect emergence, or damage to seeds, roots, shoots, or foliage of plants that are treated compared to those that are untreated.

As used herein, the term "inhibit" refers to destroy, prevent, reduce, resist, control, decrease, slow or otherwise interfere with the growth or survival of a pathogen, pest, or insect when compared to the growth or survival of the pathogen, pest, or insect in an untreated control. Any of the terms of inhibit, destroy, prevent, control, decrease, slow, interfere, resist, or reduce may be used interchangeably. In an embodiment, to "inhibit" is to destroy, prevent, control, reduce, resist, decrease, slow or otherwise interfere with the growth, emergence, or survival of a pathogen, pest, or insect by at least about 3% to at least about 100%, or any value in between for example at least about 10%, 15%, 20%, 25%, 30%, 35%, 40%, 45%, 50%, 55%, 60%, 65%, 70%, 75%, 80%, 85%, 90%, 95%, 99%, or 100% when compared to the growth or survival of the pathogen, pest, or insect in an untreated control. The amount of inhibition can be measured as described herein or by other methods known in the art. As used herein, "protects a plant, plant part or seed from a pathogen, pest, or insect pest" is intended to mean the limiting or eliminating of pathogen, pest, or insect related damage to a plant, plant part or seed by, for example, inhibiting the ability of the pathogen, pest, or insect to grow, emerge, feed, and/or reproduce or by killing the pathogen, pest, or insect. As used herein, pesticidal and/or insecticidal activity refers to an activity of a compound, a composition, and/or a method that protects a plant, a plant part or a seed from a pathogen, pest, or insect.

In an embodiment of the invention, inhibition of a pathogen, pest, or insect lasts for or provides protection for greater than a day, two days, three days, four days, five days, six days, a week, two weeks, three weeks, a month or more after an entomopathogenic fungal strain or a composition disclosed herein is applied to subject material. In another embodiment, inhibition a pathogen, pest or insect lasts from one to seven days, from seven to 14 days, from 14 to 21 days, or from 21 to 30 days or more. In another embodiment, the inhibition of the growth of a pathogen, pest, or insect lasts for or provides protection for greater than the time from application to adult emergence of the pathogen, pest, or insect.

As used herein, the term "genetically modified" or "genetically engineered" is intended to mean any species containing a genetic trait, loci, or sequence that was not found in the species or strain prior to manipulation. A genetically modified plant may be transgenic, cis-genic, genome edited, or bred to contain a genetic trait, loci, or sequence. A genetically modified plant may be prepared by means known to those skilled in the art, such as transformation by bombardment and/or bacterial mediation, by a Cas/CRISPR or TALENS system, or by breeding techniques. As used herein, a "trait" is a new or modified locus or sequence of a genetically modified plant, including but not limited to a transgenic plant. A trait may provide herbicide, pathogen, pest, or insect resistance or any other agronomically desirable characteristic, such as drought resistance or increased nitrogen utilization to the genetically modified plant.

As used herein, the term "environment of a plant, plant part or a seed" is intended to mean the area surrounding the plant, plant part or seed, including, but not limited to, the soil, the air, or in-furrow. The environment of a plant, plant part or seed may be in close proximity, touching, adjacent to, or in the same field as the plant, plant part or seed. A composition described herein may be applied to the environment of the plant, plant part or seed as a seed treatment, as a foliar application, as an in-furrow application, as a granular application, as a soil application, or as an encapsulated application. As used herein, "in-furrow" is intended to mean within or near the area where a seed is planted. A composition disclosed herein may be applied in-furrow concurrently or simultaneously with a seed. In another embodiment, a composition disclosed herein may be applied sequentially, either before or after a seed is planted.

As used herein, the term "different mode of action" is used to refer to a pesticidal composition controlling a pathogen, a pest, or an insect through a pathway or receptor that is different from another pesticidal composition. As used herein, the term "different mode of action" includes the pesticidal effects of one or more pesticidal compositions to different binding sites (i.e., different toxin receptors and/or different sites on the same toxin receptor) in the gut membranes of insects or through the RNA interference pathway to different target genes.

As used herein, the term "pathogen, pest, or insect" includes, but is not limited to, pathogenic fungi, bacteria, mites, ticks, pathogenic microorganisms, and nematodes, as well as insect from the orders Coleoptera, Lepidoptera, Mallophaga, Homoptera, Hemiptera, Orthroptera, Thysanoptera. Dermaptera, Isoptera, Anoplura, Siphonatpera, Trichoptera, and others, including but not limited to *Diabrotica virgifera virgifera, Diabrotica undecimpunctata howardi*, and *Diabrotica barberi*.

Embodiments of the present invention are useful in the inhibition of larvae and adults of the order Coleoptera from the families Anthribidae, Bruchidae and Curculionidae (including, but not limited to: *Anthonomus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *colaspis*); *Oulema melanopus* Linnaeus (cereal leaf beetle); *Zygogramma exclamationis* Fabricius (sunflower beetle); beetles from the family Coccinellidae (including, but not limited to: *Epilachna varivestis* Mulsant (Mexican bean beetle); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Methods for measuring pesticidal activity and/or the inhibition of a pathogen, pest or insect are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477, all of which are herein incorporated by reference in their entirety. Generally, the pesticide is mixed and used in feeding assays. See, for example Marrone, et al., (1985) *J. of Economic Entomology* 78:290-293. Such assays can include contacting plants with one or more pathogens, pests or insects and determining the plant's ability to survive and/or cause the death of the pathogens, pests or insects.

As used herein, the term "plant" refers to all plants, plant parts, and plant populations, such as desirable and undesirable wild plants, cultivars, transgenic plants, and plant varieties (whether or not protectable by plant variety or plant breeder's rights). Cultivars and plant varieties can be plants obtained by conventional propagation and breeding methods that can be assisted or supplemented by one or more biotechnological methods such as by use of double haploids, protoplast fusion, random and directed mutagenesis, molecular or genetic markers or by bioengineering and genetic engineering methods.

The embodiments of the invention may generally be used for any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

As used herein, the term "plant parts" refers to all above ground and below ground parts and organs of plants such as shoot, leaf, blossom and root, for example leaves, needles, stems, branches, blossoms, fruiting bodies, fruits and seeds, as well as roots, tubers, corms and rhizomes are included. Crops and vegetative and generative propagating material, for example, cuttings, corms, rhizomes, tubers, runners and seeds are also plant parts.

As used herein, the term "spore" includes, but is not limited to conidiospores, aerial conidospores, submerged spores, blastospores, spores, conidia, mycelia, vegetative mycelium, microsclerotia, and/or any other life cycle stage or mixture of life cycle stages of a fungal entomopathogen. An "aerial conidiospore" (AC) refers to conidiospores formed by the asexual developmental cycle on the surface of an agar medium, or other solid substrate of appropriate composition. As used herein, term "submerged spores" refers to submerged conidiospores and/or blastospores that develop in liquid culture.

As used herein, the term "viable" refers to a microbial cell, propagule, or spore that is metabolically active or able to grow and differentiate. Thus, propagules, such as spores, are "viable" when they are dormant and capable of germinating.

Biological control of pathogens, pests or insects of agricultural significance using a microbial agent, such as fungi, bacteria, or another species of insect or a biological compound or a biological agent derived from fungi, bacteria, insects and plants affords an environmentally friendly and commercially attractive alternative to synthetic chemical pesticides. Generally speaking, the use of biopesticides presents a lower risk of pollution and environmental hazards and biopesticides provide greater target specificity than is characteristic of traditional broad-spectrum chemical insecticides and pesticides. In addition, biopesticides often cost less to produce and thus improve economic yield for a wide variety of crops.

Certain species of microorganisms of the genus *Bacillus* are known to possess pesticidal activity against a range of insect pests including *Lepidoptera, Diptera, Coleoptera, Hemiptera* and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of Bt. These genetically modified crops are now widely used in agriculture and have provided the farmer with an environmentally friendly alternative to traditional insect-control methods. While they have proven to be very successful commercially, these genetically modified, insect-resistant crop plants provide resistance to only a narrow range of the economically important insect pests. In some cases, insects can develop resistance to different insecticidal compounds, which raises the need to identify alternative biological control agents for pathogen, pest or insect control.

An embodiment of the invention relates to an entomopathogenic fungal strain and/or a composition and a method of making and using the entomopathogenic fungal strain and/or a composition. In an embodiment the entomopathogenic strains find use in inhibiting, controlling, or killing a pathogen, pest, or insect, including, but is not limited to, fungi, pathogenic fungi, bacteria, mites, ticks, pathogenic microorganisms, and nematodes, as well as insects from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Coleoptera, including but not limited to *Diabrotica virgifera virgifera, Diabrotica undecimpunctata howardi*, and *Diabrotica barberi*, and for producing compositions with pesticidal activity.

In an embodiment, the entomopathogenic fungal strain(s) are selected from the group consisting of: *Metarhizium anisopliae* 15013-1, *Metarhizium robertsii* 23013-3, *Metarhizium anisopliae* 3213-1, and combinations thereof.

*Metarhizium anisopliae* 15013-1 (NRRL 67073) was deposited on Jun. 18, 2015 at the Agricultural Research Service Culture Collection (NRRL), 1815 North University Street, Peoria, Ill., 67073 and given accession number NRRL 67073. The deposits were made under the provisions of the Budapest Treaty on the International Recognition of the Deposit of Microorganisms for the Purposes of Patent Procedure.

*Metarhizium robertsii* 23013-3 (NRRL 67075) was deposited on Jun. 18, 2015 at the Agricultural Research Service Culture Collection (NRRL), 1815 North University Street, Peoria, Ill., 61604 and given accession number NRRL 67075. The deposits were made under the provisions of the Budapest Treaty on the International Recognition of the Deposit of Microorganisms for the Purposes of Patent Procedure.

*Metarhizium anisopliae* 3213-1 (NRRL 67074) was deposited on Jun. 18, 2015 at the Agricultural Research Service Culture Collection (NRRL), 1815 North University Street, Peoria, Ill., 61604 and given accession number NRRL 67074. The deposits were made under the provisions of the Budapest Treaty on the International Recognition of the Deposit of Microorganisms for the Purposes of Patent Procedure.

An embodiment of the invention relates to a composition comprising or consisting of or consisting essentially of an entomopathogenic fungal strain selected from the group consisting of: *Metarhizium anisopliae* 15013-1, *Metarhizium robertsii* 23013-3, and *Metarhizium anisopliae* 3213-1 and combinations thereof. In another embodiment, a composition comprises, consists of, or consists essentially of at least two or more entomopathogenic fungal strains selected from the group consisting of: *Metarhizium anisopliae* 15013-1, *Metarhizium robertsii* 23013-3, *Metarhizium anisopliae* 3213-1. In a further embodiment, a composition comprises, consists of, or consists essentially of an entomopathogenic fungal strain selected from the group consisting of: *Metarhizium anisopliae* 15013-1, *Metarhizium robertsii* 23013-3, and *Metarhizium anisopliae* 3213-1 and combinations thereof. In an embodiment, a composition is a biologically pure culture of *Metarhizium anisopliae* 15013-1, *Metarhizium robertsii* 23013-3, and *Metarhizium anisopliae* 3213-1 and combinations thereof.

An embodiment of the invention relates to a composition comprising an entomopathogenic fungal strain disclosed herein and a compound or agent selected from the group consisting of: agrochemically active compounds, biocontrol agents, lipo-chitooligosaccharide compounds (LCOs), isoflavones, quinazolines, insecticidal compounds, azolopyrimidinylamines, polymeric compounds, ionic compounds, substituted thiophenes, substituted dithiines, fluopyramm, enaminocarbonyl compounds, strigolactone compounds, and dithiino-tetracarboximide compounds and combinations thereof.

A further embodiment relates to a use of a first composition comprising an entomopathogenic fungal strain disclosed herein and a second composition comprising a compound or an agent selected from the group consisting of: agrochemically active compounds, biocontrol agents, lipo-chitooligosaccharide compounds (LCOs), isoflavones, quinazolines, insecticidal compounds, azolopyrimidinylamine, polymeric compounds, ionic compounds, substituted thiophenes, substituted dithiines, fluopyramm, enaminocarbonyl compounds, strigolactone compounds, and dithiino-tetracarboximide compounds and combinations thereof.

In an embodiment, a composition comprising an entomopathogenic fungal strain disclosed herein and a biocontrol agent is disclosed. As used herein, the term "biocontrol agent" ("BCA") includes bacteria, fungi or yeasts, protozoans, viruses, entomopathogenic nematodes, and botanical extracts, or products produced by microorganisms including proteins or secondary metabolites, and inoculants that have one or more of the following characteristics: (1) it inhibits or reduces plant infestation and/or growth of pathogens, pests, or insects, including, but not limited to, pathogenic fungi, bacteria, and nematodes, as well as arthropod pests such as insects, arachnids, chilopods, diplopods, or it inhibits plant infestation and/or growth of a combination of plant pathogens, pests, or insects; (2) it improves plant performance; (3) it improves plant yield; (4) it improves plant vigor; and (5) it improves plant health.

In an embodiment, a composition comprising an entomopathogenic fungal strain disclosed herein and an agrochemically active compounds is disclosed. Agrochemically active compounds are substances that are or may be used for treating a seed, a plant, a plant part, or the environment of a seed or a plant or a plant part including, but not limited to, fungicides, bactericides, insecticides, acaricides, nematicides, molluscicides, safeners, plant growth regulators, plant nutrients, chemical entities with a known mechanism of action, additional microorganisms, and biocontrol agents and combinations thereof.

In another embodiment, a first composition comprising an entomopathogenic fungal strain disclosed herein and a second composition comprising an agrochemically active compound, wherein the first and the second composition may inhibit plant pathogens, pests, or insects and/or improve plant performance is disclosed.

In an embodiment, a first and a second composition disclosed herein can be applied at the same time to a seed, a plant, a plant part, or the environment of a seed, a plant, or a plant part. In another embodiment, a first composition can be applied to a seed, a plant, a plant part, or the environment of a seed, a plant, or a plant part followed by application of a second composition to a seed, a plant, a plant part, or the environment of a seed, a plant, or a plant part. In yet another embodiment, a second composition can be applied to a seed, a plant, a plant part, or the environment of a seed, a plant, or a plant part followed by application of a first composition to a seed, a plant, a plant part, or the environment of a seed, a plant, or a plant part.

In an embodiment, a first and a second composition disclosed herein can be applied at the same time to a seed. In another embodiment, a first composition can be applied to a seed followed by application of a second composition to the seed. In yet another embodiment, a second composition can be applied to a seed followed by application of a first composition to the seed. In another embodiment, a first composition can be applied to a seed followed by application of a second composition to a plant. In yet another embodiment, a second composition can be applied to a seed followed by application of a first composition to a plant. In another embodiment, a first composition can be applied to a seed followed by application of a second composition to a plant part. In yet another embodiment, a second composition can be applied to a seed followed by application of a first composition to a plant part. In another embodiment, a first composition can be applied to a seed followed by application of a second composition to the environment of the seed. In yet another embodiment, a second composition can be applied to a seed followed by application of a first composition to the environment of the seed. In another embodiment, a first composition can be applied to a seed followed by application of a second composition to the environment of a plant. In yet another embodiment, a second composition can be applied to a seed followed by application of a first composition to the environment of a plant. In another embodiment, a first composition can be applied to a seed followed by application of a second composition to the environment of a plant part. In yet another embodiment, a second composition can be applied to a seed followed by application of a first composition to the environment of a plant part.

In an embodiment, a first and a second composition disclosed herein can be applied at the same time to a plant. In another embodiment, a first composition can be applied to a plant followed by application of a second composition to the plant. In yet another embodiment, a second composition can be applied to a plant followed by application of a first composition to the plant. In another embodiment, a first composition can be applied to a plant followed by application of a second composition to a seed. In yet another embodiment, a second composition can be applied to a plant followed by application of a first composition to a seed. In another embodiment, a first composition can be applied to a plant followed by application of a second composition to a plant part. In yet another embodiment, a second composition can be applied to a plant followed by application of a first composition to a plant part. In another embodiment, a first composition can be applied to a plant followed by application of a second composition to the environment of a seed. In yet another embodiment, a second composition can be applied to a plant followed by application of a first composition to the environment of a seed. In another embodiment, a first composition can be applied to a plant followed by application of a second composition to the environment of the plant. In yet another embodiment, a second composition can be applied to a plant followed by application of a first composition to the environment of the plant. In another embodiment, a first composition can be applied to a plant followed by application of a second composition to the environment of a plant part. In yet another embodiment, a second composition can be applied to a plant followed by application of a first composition to the environment of a plant part.

In an embodiment, a first and a second composition disclosed herein can be applied at the same time to a plant part. In another embodiment, a first composition can be applied to a plant part followed by application of a second composition to the plant part. In yet another embodiment, a second composition can be applied to a plant part followed by application of a first composition to the plant part. In another embodiment, a first composition can be applied to a plant part followed by application of a second composition to a seed. In yet another embodiment, a second composition can be applied to a plant part followed by application of a first composition to a seed. In another embodiment, a first composition can be applied to a plant part followed by application of a second composition to a plant. In yet another embodiment, a second composition can be applied to a plant part followed by application of a first composition to a plant. In another embodiment, a first composition can be applied to a plant part followed by application of a second composition to the environment of a seed. In yet another embodiment, a second composition can be applied to a plant part followed by application of a first composition to the environment of a seed. In another embodiment, a first composition can be applied to a plant part followed by application of a second composition to the environment of a plant. In yet another embodiment, a second composition can be applied to a plant part followed by application of a first composition to the environment of a plant. In another embodiment, a first composition can be applied to a plant part followed by application of a second composition to the environment of the plant part. In yet another embodiment, a second composition can be applied to a plant part followed by application of a first composition to the environment of the plant part.

In an embodiment, a first and a second composition disclosed herein can be applied at the same time to the environment of a seed. In another embodiment, a first composition can be applied to the environment of a seed followed by application of a second composition to the environment of the seed. In yet another embodiment, a second composition can be applied to the environment of a seed followed by application of a first composition to the environment of the seed. In another embodiment, a first composition can be applied to the environment of a seed followed by application of a second composition to a seed. In yet another embodiment, a second composition can be applied to the environment of a seed followed by application of a first composition to a seed. In another embodiment, a first composition can be applied to the environment of a seed followed by application of a second composition to a plant. In yet another embodiment, a second composition can be applied to the environment of a seed followed by application of a first composition to a plant. In another embodiment, a first composition can be applied to the environment of a seed followed by application of a second composition to a plant part. In yet another embodiment, a second composition can be applied to the environment of a seed followed by application of a first composition to a plant part. In another embodiment, a first composition can be applied to the environment of a seed followed by application of a second composition to the environment of a plant. In yet another embodiment, a second composition can be applied to the environment of a seed followed by application of a first composition to the environment of a plant. In another embodiment, a first composition can be applied to the environment of a seed followed by application of a second composition to the environment of a plant part. In yet another embodiment, a second composition can be applied to the environment of a seed followed by application of a first composition to the environment of a plant part.

In an embodiment, a first and a second composition disclosed herein can be applied at the same time to the environment of a plant. In another embodiment, a first composition can be applied to the environment of a plant followed by application of a second composition to the environment of the plant. In yet another embodiment, a second composition can be applied to the environment of a plant followed by application of a first composition to the environment of the plant. In another embodiment, a first composition can be applied to the environment of a plant followed by application of a second composition to a seed. In yet another embodiment, a second composition can be applied to the environment of a plant followed by application of a first composition to a seed. In another embodiment, a first composition can be applied to the environment of a plant followed by application of a second composition to a plant. In yet another embodiment, a second composition can be applied to the environment of a plant followed by application of a first composition to a plant. In another embodiment, a first composition can be applied to the environment of a plant followed by application of a second composition to a plant part. In yet another embodiment, a second composition can be applied to the environment of a plant followed by application of a first composition to a plant part. In another embodiment, a first composition can be applied to the environment of a plant followed by application of a second composition to the environment of a seed. In yet another embodiment, a second composition can be applied to the environment of a plant followed by application of a first composition to the environment of a seed. In another embodiment, a first composition can be applied to the environment of a plant followed by application of a second composition to the environment of a plant part. In yet another embodiment, a second composition can be applied to the environment of a plant followed by application of a first composition to the environment of a plant part.

In an embodiment, a first and a second composition disclosed herein can be applied at the same time to the environment of a plant part. In another embodiment, a first composition can be applied to the environment of a plant part followed by application of a second composition to the environment of the plant part. In yet another embodiment, a second composition can be applied to the environment of a plant part followed by application of a first composition to the environment of the plant part. In another embodiment, a first composition can be applied to the environment of a plant part followed by application of a second composition to a seed. In yet another embodiment, a second composition can be applied to the environment of a plant part followed by application of a first composition to a seed. In another embodiment, a first composition can be applied to the environment of a plant part followed by application of a second composition to a plant. In yet another embodiment, a second composition can be applied to the environment of a plant part followed by application of a first composition to a plant. In another embodiment, a first composition can be applied to the environment of a plant part followed by application of a second composition to the environment of a seed. In yet another embodiment, a second composition can be applied to the environment of a plant part followed by application of a first composition the environment of a seed. In another embodiment, a first composition can be applied to the environment of a plant part followed by application of a second composition to the environment of a plant. In yet another embodiment, a second composition can be applied to the environment of a plant part followed by application of a first composition to the environment of a plant.

In an embodiment, the use of an entomopathological fungal strain disclosed herein with a composition comprising an insecticidal protein from *Pseudomonas* sp. such as PSEEN3174 (Monalysin; (2011) *PLoS Pathogens* 7:1-13); from *Pseudomonas protegens* strain CHA0 and Pf-5 (previously *fluorescens*) (Pechy-Tarr, (2008) *Environmental Microbiology* 10:2368-2386; GenBank Accession No. EU400157); from *Pseudomonas Taiwanensis* (Liu, et al., (2010) *J. Agric. Food Chem.*, 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxicology Journal*, 3:101-118 and Morgan, et al., (2001) *Applied and Envir. Micro.* 67:2062-2069); U.S. Pat. Nos. 6,048,838, and 6,379,946; a PIP-1 polypeptide of US Patent Publication US20140007292; an AfIP-1A and/or AfIP-1B polypeptide of US Patent Publication US20140033361; a PHI-4 polypeptide of U.S. Ser. No. 13/839,702; a PIP-47 polypeptide of PCT Serial Number PCT/US14/51063, a PIP-72 polypeptide of PCT Serial Number PCT/US14/55128, and S-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry 28, Cry 29, Cry 30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry 51 and Cry55 classes of δ-endotoxin genes and the *B. thuringiensis* cytolytic Cyt1 and Cyt2 genes is disclosed.

In an embodiment, a composition disclosed herein comprises a silencing construct of a polynucleotide of interest resulting in suppression of a target pathogen, pest, or insect polypeptides. By "silencing element" is it intended to mean a polynucleotide which when contacted by or ingested by a pest, is capable of reducing or eliminating the level or expression of a target polynucleotide or the polypeptide encoded thereby. The silencing element employed can reduce or eliminate the expression level of the target sequence by influencing the level of the target RNA transcript or, alternatively, by influencing translation and thereby affecting the level of the encoded polypeptide. Silencing elements may include, but are not limited to, a sense suppression element, an antisense suppression element, a double stranded RNA, a siRNA, an amiRNA, a miRNA, or a hairpin suppression element.

In another embodiment, a composition disclosed herein comprises nucleic acid molecules including silencing elements for targeting the vacuolar ATPase H subunit, useful for controlling a coleopteran pest population and infestation as described in US Patent Application Publication 2012/0198586. In an embodiment, a composition disclosed herein comprises ribonucleic acid (RNA or double stranded RNA) that inhibits or down regulates the expression of a target gene that encodes: an insect ribosomal protein such as the ribosomal protein L19, the ribosomal protein LAO or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein as described in PCT Publication WO 2012/055982. In another embodiment, a composition disclosed herein comprises ribonucleic acid (RNA or double stranded RNA) that inhibits or down regulates the expression of a target gene that encodes Snf7 as described in PCT publication WO 2007/035650. In an embodiment, a composition disclosed herein comprises polynucleotide silencing elements targeting RPS10 described in US Patent Application publication 2011/0054007. In another embodiment, a composition disclosed herein comprises polynucleotide silencing elements targeting RyanR and PAT3 described in US Patent Application publications 2014/0275208 and US2015/0257389. In an embodiment, a composition disclosed herein comprises interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene as described in US Patent Application Publications 2012/029750, US 20120297501, and 2012/0322660. In another embodiment, a composition disclosed herein comprises potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubulin Homologous Sequence as described in US Patent Application Publication 2012/0164205.

An embodiment of the invention comprises an additional component, which may be a carrier, an adjuvant, a solubilizing agent, a suspending agent, a diluent, a stabilizer, an oxygen scavenger, an antioxidant, a food material, an anti-contaminant agent, or combinations thereof.

In another embodiment, an additional component(s) may be required for an application to which an entomopathogenic fungal strain or a composition disclosed herein is to be utilized. For example, if a strain or a composition is to be utilized on, or in, an agricultural product, the additional component(s) may be an agriculturally acceptable carrier, an excipient, or a diluent and combinations thereof. Likewise, if a strain or a composition is to be utilized on, or in, a foodstuff the additional component(s) may be an edible carrier, excipient or diluent and combinations thereof.

"Carriers" or "vehicles" mean materials suitable for compound administration and include any such materials known in the art such as, for example, any liquid, gel, solvent, liquid diluent, solubilizer, or the like, which is non-toxic and does not interact with any components of a composition in a deleterious manner.

Examples of nutritionally acceptable or edible carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethylcellulose, polyvinylpyrrolidone, and the like and combinations thereof.

Examples of excipients include, but are not limited to, microcrystalline cellulose and other celluloses, lactose, sodium citrate, calcium carbonate, dibasic calcium phosphate, glycine, starch, milk sugar, and high molecular weight polyethylene glycols and combinations thereof.

Examples of diluents include, but are not limited to, water, ethanol, propylene glycol and glycerin, and combinations thereof.

Additional components may be used simultaneously with an entomopathogenic fungal strain and/or a composition disclosed herein (e.g. when they are in admixture together or even when they are delivered by different routes) or sequentially (e.g. they may be delivered by different routes).

An entomopathogenic fungal strain and/or a composition disclosed herein and/or its diluent may also contain chelating agents such as EDTA, citric acid, tartaric acid, etc. Moreover, an entomopathogenic fungal strain and/or a composition disclosed herein and/or its diluent may contain active agents selected from fatty acids esters, such as mono- and diglycerides, non-ionic surfactants, such as polysorbates, phospholipids, etc. An entomopathogenic fungal strain and/or a composition disclosed herein and/or its diluent may also contain emulsifiers, which may enhance the stability of an entomopathogenic fungal strain and/or a composition, especially after dilution.

An entomopathogenic fungal strain and/or a composition disclosed herein may be used in any suitable form, whether when used alone or when present in a composition. An entomopathogenic fungal strain and/or a composition disclosed herein may be formulated in any suitable way to ensure that the composition comprises an active entomopathogenic fungal strain.

An entomopathogenic fungal strain and/or a composition hereof may be in the form of a dry powder that can be sprinkled on or mixed in with a product. Entomopathogenic fungal strains and/or compositions of the embodiments of the invention disclosed herein in the form of a dry powder may include an additive such as microcrystalline cellulose, gum tragacanth, gelatin, starch, lactose, alginic acid, Primojel®, or corn starch (which can be used as a disintegrating agent).

In yet another embodiment, an entomopathogenic fungal strain and/or a composition disclosed herein can be a spray-dried fermentate re-suspended in $H_2O$ to a percentage selected from the following: 0.05-1, 1-3, 3-5, 5-7, 7-10, 10-15, 15-20, and greater than 20%. In another embodiment, a clarification step(s) can be performed prior to spray-drying.

In an embodiment, compositions disclosed herein can comprise a suspension of propagules, such as spores, from an entomopathogenic fungal strain disclosed herein. In an embodiment, a suspension of propagules, such as spores, can be in a range of $1\times10^3$ to $1\times10^{13}$ CFU/ml.

In an embodiment, compositions disclosed herein can comprise concentrated, dried propagules, such as spores, from an entomopathogenic fungal strain disclosed herein. In an embodiment, concentrated, dried spores can be in a range of $1\times10^3$ to $1\times10^{10}$ CFU/g.

In an embodiment, an entomopathogenic fungal strain and/or a composition disclosed herein can be applied in a wet or a partially or a completely desiccated form or in a slurry, a gel, or another form.

In at least some embodiments, an entomopathogenic fungal strain and/or a composition disclosed herein can be freeze-dried or lypholized. In at least some embodiments, an entomopathogenic fungal strain and/or a composition disclosed herein can be mixed with a carrier. A carrier includes, but is not limited to, whey, maltodextrin, sucrose, dextrose, limestone (calcium carbonate), rice hulls, yeast culture, dried starch, clay, and sodium silico aluminate. However, it is not necessary to freeze-dry an entomopathogenic fungal strain and/or a composition disclosed herein before using it. An entomopathogenic fungal strain and/or a composition disclosed herein can also be used with or without preservatives and in a concentrated, an un-concentrated, or a diluted form. In an embodiment, an entomopathogenic fungal strain and/or a composition disclosed herein can be in the form of a pellet or a biologically pure pellet.

An entomopathogenic fungal strain and/or a composition disclosed herein can be added to a carrier. Where used, the carrier(s) and an entomopathogenic fungal strain and/or a composition disclosed herein can be added to a ribbon or paddle mixer and mixed for about 15 minutes, although the timing can be increased or decreased. The components are blended such that a uniform mixture of an entomopathogenic fungal strain and/or a composition disclosed herein and carrier(s) is produced. The final product is preferably a dry, flowable powder.

In an embodiment, an entomopathogenic fungal strain and/or a composition may be formulated as a liquid, a dry powder, or a granule. A dry powder or granules may be prepared by means known to those skilled in the art, such as, in a top-spray fluid bed coater, in a bottom spray Wurster, or by a drum granulation (e.g. high sheer granulation), an extrusion, a pan coating or in a micro-ingredients mixer.

In another embodiment, an entomopathogenic fungal strain and/or a composition may be provided as a spray-dried or a freeze-dried powder.

In yet another embodiment, an entomopathogenic fungal strain and/or a composition is in a liquid formulation. Such liquid formulation may contain one or more of the following: a buffer, a salt, sorbitol, and/or glycerol.

In an embodiment, an entomopathogenic fungal strain and/or a composition disclosed herein may be formulated with a physiologically acceptable carrier selected from maltodextrin, calcined (illite) clay, limestone (calcium carbonate), cyclodextrin, wheat or a wheat component, sucrose, starch, $Na_2SO_4$, talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

In an embodiment, an entomopathogenic fungal strain and/or a composition disclosed herein may be formulated by encapsulation technology to improve fungal propagule, such as spores, stability and as a way to protect the fungal propagules from seed applied fungicides. In an embodiment the encapsulation technology may comprise a bead polymer for timed release of fungal propagules, such as spores, over time. In an embodiment, an encapsulated entomopathogenic fungal strain and/or a composition may be applied in a separate application of beads in-furrow to the seeds. In another embodiment, an encapsulated entomopathogenic fungal strain and/or a composition may be co-applied simultaneously with seeds.

A coating agent usable for the sustained release of microparticles of an encapsulation embodiment of an entomopathogenic fungal strain and/or a composition disclosed herein may be a substance which is useful for coating a microgranular form with the substance to be supported thereon. Any coating agent which can form a coating difficulty permeable for the supported substance may be used in general, without any particular limitation. For example, higher saturated fatty acid, wax, thermoplastic resin, thermosetting resin and the like may be used.

Examples of useful higher saturated fatty acids include stearic acid, zinc stearate, stearic acid amide and ethylen-ebis-stearic acid amide. Examples of waxes include synthetic waxes such as polyethylene wax, carbon wax, Hoechst wax, and fatty acid ester; natural waxes such as carnauba wax, bees wax and Japan wax; and petroleum waxes such as paraffin wax and petrolatum. Examples of thermoplastic resins include acrylic ester resin, polyolefins such as polyethylene, polypropylene, polybutene and polystyrene; vinyl polymers such as polyvinyl acetate, polyvinyl chloride, polyvinylidene chloride, polyacrylic acid, polymethacrylic acid, polyacrylate and polymethacrylate; diene polymers such as butadiene polymer, isoprene polymer, chloroprene polymer, butadiene-styrene copolymer, ethylene-propylene-diene copolymer, styrene-isoprene copolymer, MMA-butadiene copolymer and acrylonitrile-butadiene copolymer; polyolefin copolymers such as ethylene-propylene copolymer, butene-ethylene copolymer, butene-propylene copolymer, ethylene-vinyl acetate copolymer, ethylene-acrylic acid copolymer, styreneacrylic acid copolymer, ethylene-methacrylic acid copolymer, ethylene-methacrylic ester copolymer, ethylene-carbon monoxide copolymer, ethylene-vinyl acetate-carbon monoxide copolymer, ethylene-vinyl acetate-vinyl chloride copolymer and ethylene-vinyl acetate-acrylic copolymer; and vinyl chloride copolymers such as vinyl chloride-vinyl acetate copolymer and vinylidene chloride-vinyl chloride copolymer. Examples of thermosetting resins include polyurethane resin, epoxy resin, alkyd resin, unsaturated polyester resin, phenolic resin, urea-melamine resin, urea resin and silicone resin. Of these resins, thermoplastic acrylic ester resin, butadiene-styrene copolymer resin, thermosetting polyurethane resin and epoxy resin are preferred, and among these preferred resins, thermosetting polyurethane resin is particularly preferred. These coating agents can be used either singly or in combinations.

In an embodiment, an entomopathogenic fungal strain and/or a composition can include a seed, a part of a seed, a plant, or a plant part.

All plants, plant parts, seeds, seed parts or soil can be treated with an entomopathogenic fungal strain and/or a composition and by a method disclosed herein. A composition disclosed herein can include a plant, a plant part, a seed, a seed part, soil, or the environment of a plant, a plant part, a seed, or a seed part. An entomopathogenic fungal strain, a composition, and a method disclosed herein can be applied to a seed, a seed part, a plant, a plant part, a fruit, the environment of a seed, a seed part, a plant, a plant part, or a fruit, or the soil in which a seed, a seed part, a plant, a plant part or a fruit grows.

An embodiment of the invention relates to a method for reducing plant pathogen, pest, or insect damage to a seed, a plant or a plant part comprising: (a) treating a seed with an entomopathogenic fungal strain and/or a composition disclosed herein prior to planting. In another embodiment, the method further comprises: (b) treating a plant, a plant part, or the environment of a plant or a plant part obtained from the seed with an entomopathogenic fungal strain and/or a composition disclosed herein. The entomopathogenic fungal strain and/or the composition used in step (a) may be the same as or different from the entomopathogenic fungal strain or the composition used in step (b).

An embodiment of the invention relates to a method for reducing plant pathogen, pest, or insect damage to a seed, a plant or a plant part comprising: (a) treating the soil surrounding a seed, a plant or a plant part with an entomopathogenic fungal strain or a composition disclosed herein. In another embodiment, the method further comprises: (b) treating a seed, a plant a plant part, or the environment of a seed, a plant or a plant panr with an entomopathogenic fungal strain or a composition disclosed herein. The entomopathogenic fungal strain or the composition used in step (a) may be the same as or different from the entomopathogenic fungal strain or the composition used in step (b).

An embodiment of the invention relates to a method for reducing plant pathogen, pest, or insect damage to a seed, a plant or a plant part comprising: (a) treating a seed prior to planting with an entomopathogenic fungal strain or a composition disclosed herein. In another embodiment, the method further comprises: (b) treating the soil surrounding a seed, a plant or a plant part or the environment of a plant or a plant part with an entomopathogenic fungal strain or a composition disclosed herein. In still another embodiment, the method further comprises: (c) treating a plant, a plant part, or the environment of a plant or a plant part of a plant produced from the seed with an entomopathogenic fungal strain or a composition disclosed herein. The entomopathogenic fungal strain or the composition used in step (a) may be the same as or different from the entomopathogenic fungal strain or the composition used in step (b). The entomopathogenic fungal strain or the composition used in step (a) may be the same as or different from the entomopathogenic fungal strain or the composition used in step (c). The entomopathogenic fungal strain or the composition used in step (b) may be the same as or different from the entomopathogenic fungal strain or the composition used in step (c).

In an embodiment, wild plant species and plant cultivars, or those obtained by conventional biological breeding, such as crossing or protoplast fusion, seeds and plant parts thereof, can be treated with an entomopathogenic fungal strain and/or a composition and a method disclosed herein. In another embodiment, transgenic plants and plant cultivars obtained by genetic engineering, seeds and plant parts thereof, can be treated with an entomopathogenic fungal strain and/or a composition and a method disclosed herein.

In another embodiment, a seed, a plant, a plant part or a plant cultivar (obtained by plant biotechnology methods such as genetic engineering) that may be treated with an entomopathogenic fungal strain and/or a composition and a method disclosed herein are herbicide-tolerant or herbicide-resistant plants, i.e. plants made tolerant or resistant to one or more herbicides. Such plants can be obtained either by genetic modification, or by selection of plants containing a mutation imparting such herbicide tolerance or resistance. Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshilcimate-3-phosphate synthase (EPSPS).

Seeds, plants, plant parts or plant cultivars (obtained by plant biotechnology methods such as genetic engineering) that may also be treated with an entomopathogenic fungal strain and/or a composition and a method disclosed herein are insect-resistant genetically modified plants (or transgenic plants), i.e. plants made resistant to attack by certain target insects. Such seeds, plants, plant parts or plant cultivars can be obtained by genetic transformation, or by selection of plants containing a mutation imparting such insect resistance.

In another embodiment, seeds, plants, plant parts, or plant cultivars (obtained by plant biotechnology methods such as genetic engineering) that may be treated with an entomopathogenic fungal strain and/or a composition and a method disclosed herein are tolerant to abiotic stresses. Such seeds, plants, plant parts, or plant cultivars can be obtained by genetic transformation, or by selection of seeds, plants, plant parts, or plant cultivars containing a mutation imparting such stress resistance.

In another embodiment, seeds, plants, plant parts, or plant cultivars (obtained by plant biotechnology methods such as genetic engineering) that may be treated with an entomopathogenic fungal strain and/or a composition and a method disclosed herein are conventionally bred, produced by mutagenesis, or genetically engineered to contain a combination or stack of valuable traits, including, but not limited to, herbicide tolerance, insect resistance, and abiotic stress tolerance. The entomopathogenic fungal strains, compositions and methods of the embodiments of the invention may be used to treat plant varieties which will be developed, or marketed, in the future and which have these genetic traits or traits to be developed in the future.

As used herein, applying an entomopathogenic fungal strain or a composition to a seed, a plant, or plant part, or the environment of a seed, a plant or a plant part includes contacting the seed, the plant, or the plant part, or the environment of the seed, the plant or the plant part directly and/or indirectly with the entomopathogenic fungal strains or the compositions disclosed herein. In an embodiment, an entomopathogenic fungal strain or a composition may be directly applied to a seed, a plant or a plant part, or the environment of a seed, a plant or a plant part as a spray, a rinse, or a powder, or any combination thereof. A contacting step may occur while a seed, a plant or a plant part is being grown, while a plant or a plant part is being fertilized, while a plant or a plant part is being harvested, after a plant or a plant part has been harvested, while a plant or a plant part is being processed, while a plant or a plant part is being packaged, or while a plant or a plant part is being stored in a warehouse or on a shelf in a store.

As used herein, a spray refers to a mist of liquid particles that contains an entomopathogenic fungal strain or a composition of an embodiment disclosed herein. In an embodiment, a spray containing an entomopathogenic fungal strain or a composition of an embodiment disclosed herein may be applied to a seed prior to or at the time of planting. In an embodiment, a spray may be applied to a plant or a plant part while the plant or the plant part is being grown. In another embodiment, a spray may be applied to a plant or a plant part while the plant or the plant part is being fertilized. In another embodiment, a spray may be applied to a plant or a plant part while the plant or the plant part is being harvested. In another embodiment, a spray may be applied to a plant or a plant part after the plant or the plant part has been harvested. In another embodiment, a spray may be applied to a plant or a plant part while the plant or the plant part is being processed. In another embodiment, a spray may be applied to a plant or a plant part while the plant or the plant part is being packaged. In another embodiment, a spray may be applied to a plant or a plant part while the plant or the plant part is being stored.

In another embodiment, an entomopathogenic fungal strain or a composition disclosed herein may be applied directly to a seed, a plant or a plant part, or the environment of a seed, a plant or a plant part as a rinse. As used herein, a rinse is a liquid containing an entomopathogenic fungal strain or a composition disclosed herein. Such a rinse may be poured over a seed, a plant or a plant part or the environment of a seed, a plant or a plant part. A seed, a plant or a plant part may also be immersed or submerged in the rinse, then removed and allowed to dry.

In another embodiment, an entomopathogenic fungal strain or a composition disclosed herein may be applied to a seed, a plant or a plant part or the environment of a seed, a plant or a plant part and may cover 50% of the surface area of the seed, the plant or the plant part or the environment of a seed, a plant or a plant part. In another embodiment, an entomopathogenic fungal strain or a composition may be applied to a seed, a plant or a plant part or the environment of a seed, a plant or a plant part and may cover a percentage of the surface area of the seed, the plant or the plant part or the environment of a seed, a plant or a plant part selected from the group consisting of: from 50% to about 95%, from 60% to about 95%, from 70% to about 95%, from 80% to about 95%, and from 90% to about 95%.

In another embodiment, an entomopathogenic fungal strain or a composition disclosed herein may cover from about 20% to about 30%, from about 30% to about 40%, from about 40% to about 50%, from about 50% to about 60%, from about 60% to about 70%, from about 70% to about 80%, from about 80% to about 90%, from about 90% to about 95%, from about 95% to about 98%, from about 98% to about 99% or 100% of the surface area of a seed, a plant or a plant part or the environment of a seed, a plant or a plant part.

In another embodiment, an entomopathogenic fungal strain or a composition disclosed herein may be applied directly to a seed, a plant or a plant part or the environment of a seed, a plant or a plant part as a powder. As used herein, a powder is a dry or nearly dry bulk solid composed of a large number of very fine particles that may flow freely when shaken or tilted. A dry or a nearly dry powder composition disclosed herein preferably contains a low percentage of water, such as, for example, less than 5%, less than 2.5%, or less than 1% by weight.

In another embodiment, an entomopathogenic fungal strain and/or a composition disclosed herein can be applied indirectly to a seed, a plant or a plant part or the environment of a seed, a plant or a plant part. For example, a seed, a plant or a plant part or the environment of a seed, a plant or a plant part having an entomopathogenic fungal strain and/or a composition disclosed herein already applied may be touching another seed, another plant or another plant part so that an entomopathogenic fungal strain or a composition rubs off on the other seed, plant or plant part. In a further embodiment, an entomopathogenic fungal strain or a composition disclosed herein may be applied using an applicator. In some embodiments, an applicator may include, but is not limited to, a syringe, a sponge, a paper towel, or a cloth, or any combination thereof.

In another embodiment, an entomopathogenic fungal strain and/or a composition disclosed herein may be a colloidal dispersion. A colloidal dispersion is a type of chemical mixture where one substance is dispersed evenly throughout another. Particles of the dispersed substance are only suspended in the mixture, unlike a solution, where they are completely dissolved within a solvent. This occurs because the particles in a colloidal dispersion are larger than the particles in a solution, they are small enough to be dispersed evenly and to maintain a homogenous appearance, but are large enough to scatter light and not dissolve. Colloidal dispersions are an intermediate between homogeneous and heterogeneous mixtures and are sometimes classified as either "homogeneous" or "heterogeneous" based upon their appearance.

In an embodiment, an entomopathogenic fungal strain, a composition, and a method disclosed herein are suitable for use with a seed. In another embodiment, an entomopathogenic fungal strain, a composition, and a method disclosed herein are suitable for use with a seed of one or more of any of the plants or the plant parts recited previously.

In still another embodiment, an entomopathogenic fungal strain, a composition and a method disclosed herein can be used to treat transgenic or genetically modified seed. A transgenic seed refers to the seed of plants containing at least one heterologous gene that allows the expression of a polypeptide or protein not naturally found in the plant. The heterologous gene in transgenic seed can originate, for example, from microorganisms of the species *Bacillus, Rhizobium, Pseudomonas, Serratia, Trichoderma, Clavibacter, Glomus* or *Gliocladium.*

In an embodiment, a seed is treated in a state in which it is sufficiently stable so that the treatment does not cause any damage. In general, treatment of a seed may take place at any point in time between harvesting and sowing. In an embodiment, a seed to be treated with an entomopathogenic fugal strain, a composition or a method disclosed herein is separated from a plant and freed from cobs, shells, stalks, coats, hairs or flesh of a fruit. Thus, it is possible to use, for example, a seed which has been harvested, cleaned and dried. Alternatively, it is also possible to use a seed which, after drying, has been treated, for example, with water and then dried again.

In an embodiment, a seed is treated with an entomopathogenic fungal strain, a composition and a method disclosed herein in such a way that the germination of the seed is not adversely affected and/or a resulting plant is not damaged.

In an embodiment, an entomopathogenic fungal strain, a composition, and a method disclosed herein can be applied directly to a seed. For example, an entomopathogenic fungal strain, a composition and a method disclosed herein can be applied without additional components and without having been diluted.

In another embodiment, an entomopathogenic fungal strain, and/or a composition disclosed herein are applied to a seed in the form of a suitable formulation. Suitable formulations and methods for the treatment of a seed are known to the person skilled in the art and are described, for example, in the following documents: U.S. Pat. Nos. 4,272,417 A, 4,245,432 A, 4,808,430 A, 5,876,739 A, US 2003/0176428 A1. WO 2002/080675 A1. WO 2002/028186 A2.

An entomopathogenic fungal strain and/or a composition disclosed herein can be converted into customary seed dressing formulations, such as solutions, emulsions, suspensions, powders, foams, slurries, colloidal dispersions or other coating materials for seed, and also ULV formulations. These formulations are prepared in a known manner by mixing an entomopathogenic fungal strain and/or a composition disclosed herein with customary additives, such as, for example, customary extenders and also solvents or diluents, colorants, wetting agents, dispersants, emulsifiers, defoamers, preservatives, secondary thickeners, adhesives, gibberellins and water as well.

In another embodiment, suitable colorants may be present in a seed dressing formulation including all colorants customary for such purposes. Use may be made both of pigments, which have sparing solubility in water, and of dyes, which are soluble in water. Examples include the colorants known under the designations Rhodamine B, C.I. Pigment Red 112, and C.I. Solvent Red 1.

In another embodiment, suitable wetting agents may be present in a seed dressing formulation, including all substances that promote wetting in a formulation of active agrochemical substances. The use of alkylnaphthalene-sulphonates, such as diisopropyl- or diisobutylnaphthalenesulphonates are preferred.

In still another embodiment, suitable dispersants and/or emulsifiers may be present in a seed dressing formulation including all nonionic, anionic, and cationic dispersants. In an embodiment, nonionic or anionic dispersants or mixtures of nonionic or anionic dispersants can be used. In an embodiment, nonionic dispersants include, but are not limited to, ethylene oxide-propylene oxide block polymers, alkylphenol polyglycol ethers, and tristyrylphenol polyglycol ethers, and their phosphated or sulphated derivatives.

In still another embodiment, defoamers may be present in a seed dressing formulation incorporating an entomopathogenic fungal strain and/or a composition of an embodiment of the invention including all foam-inhibiting compounds including, but not limited to, silicone defoamers, magnesium stearate, silicone emulsions, long-chain alcohols, fatty acids and their salts, and organofluorine compounds and mixtures thereof.

In still another embodiment, secondary thickeners may be present in a seed dressing formulation including all compounds which can be used for such purposes in an agrochemical composition, including, but not limited to, cellulose derivatives, acrylic acid derivatives, polysaccharides, such as xanthan gum or Veegum®, modified clays, phyllosilicates, such as attapulgite and bentonite, and also finely divided silicic acids.

In another embodiment, adhesives may be present in a seed dressing formulation incorporating an entomopathogenic fungal strain and/or a composition disclosed herein including all customary binders which can be used in seed dressings. Polyvinylpyrrolidone, polyvinyl acetate, polyvinyl alcohol and tylose are preferred.

In yet another embodiment, a seed dressing formulation incorporating an entomopathogenic fungal strain and/or a composition disclosed herein may be used directly or after dilution with water to treat a seed of any seed type. A seed dressing formulation or its dilute preparation may also be used to dress a seed of transgenic plants. In this context, synergistic effects may arise in interaction of the seed dressing formulation with substances formed by transgenic expression.

Suitable mixing equipment for treating a seed with a seed dressing formulation or preparations prepared from them by adding water includes all mixing equipment that can commonly be used for dressing. The specific procedure adopted when dressing comprises introducing a seed into a mixer, adding a particular desired amount of a seed dressing formulation, either as it is or following dilution with water, and carrying out mixing until the formulation is uniformly distributed on the seed. Optionally, a drying operation follows the treating operation.

In an embodiment, an entomopathogenic fungal strain and/or a composition or a formulation disclosed herein can be added to a plant, a plant part, and/or a seed at a rate of about $1 \times 10^3$ to $1 \times 10^{13}$ colony forming units (cfu) per seed, including about $1 \times 10^3$ cfu/seed, or about $1 \times 10^4$ cfu/seed, $1 \times 10^5$ cfu/seed, or about $1 \times 10^6$ cfu/seed, or about $1 \times 10^7$ cfu/seed, or about $1 \times 10^8$ cfu/seed, or about $1 \times 10^9$ cfu/seed, or about $1 \times 10^{10}$ cfu/seed, or about $1 \times 10^{11}$ cfu/seed, or about $1 \times 10^{12}$ cfu/seed, or about $1 \times 10^{13}$ cfu/seed including about $1 \times 10^3$ to $1 \times 10^8$ cfu/seed about $1 \times 10^3$ to $1 \times 10^7$ cfu/seed, about $1 \times 10^3$ to $1 \times 10^5$ cfu/seed, about $1 \times 10^3$ to $1 \times 10^6$ cfu/seed, about $1 \times 10^3$ to $1 \times 10$ cfu/seed, about $1 \times 10^3$ to $1 \times 10^9$ cfu/seed, about $1 \times 10^3$ to $1 \times 10^{10}$ cfu/seed, about $1 \times 10^3$ to $1 \times 10^{11}$ cfu/seed, about $1 \times 10^3$ to $1 \times 10^{12}$ cfu/seed, about $1 \times 10^3$ to $1 \times 10^{13}$ cfu/seed, about $1 \times 10^4$ to $1 \times 10^8$ cfu/seed about $1 \times 10^4$ to $1 \times 10^7$ cfu/seed, about $1 \times 10^4$ to $1 \times 10^5$ cfu/seed, about $1 \times 10^4$ to $1 \times 10^6$ cfu/seed, about $1 \times 10^4$ to $1 \times 10^9$ cfu/seed, about $1 \times 10^4$ to $1 \times 10^{10}$ cfu/seed, about $1 \times 10^{11}$ to $1 \times 10^9$ cfu/seed, about $1 \times 10^4$ to $1 \times 10^{12}$ cfu/seed about $1 \times 10^4$ to $1 \times 10^{13}$ cfu/seed, about $1 \times 10^5$ to $1 \times 10^7$ cfu/per seed, about $1 \times 10^5$ to $1 \times 10^6$ cfu/per seed, about $1 \times 10^5$ to $1 \times 10^8$ cfu/per seed, about $1 \times 10^5$ to $1 \times 10^9$ cfu/per seed, about $1 \times 10^5$ to $1 \times 10^{10}$ cfu/per seed, about $1 \times 10^5$ to $1 \times 10^{11}$ cfu/per seed, about $1 \times 10^5$ to $1 \times 10^{12}$ cfu/per seed, about $1 \times 10^5$ to $1 \times 10^{13}$ cfu/per seed, about $1 \times 10^6$ to $1 \times 10^8$ cfu/per seed, about $1 \times 10^6$ to $1 \times 10^7$ cfu/per seed, about $1 \times 10^6$ to $1 \times 10^9$ cfu/per seed, about $1 \times 10^6$ to $1 \times 10^{10}$ cfu/per seed, about $1 \times 10^6$ to $1 \times 10^{11}$ cfu/per seed, about $1 \times 10^6$ to $1 \times 10^{12}$ cfu/per seed, about $1 \times 10^6$ to $1 \times 10^{13}$ cfu/per seed, about $1 \times 10^7$ to $1 \times 10^8$ cfu/per seed, about $1 \times 10^7$ to $1 \times 10^9$ cfu/per seed, about $1 \times 10^7$ to $1 \times 10^{10}$ cfu/per seed, about $1 \times 10^7$ to $1 \times 10^{11}$ cfu/per seed, about $1 \times 10^7$ to $1 \times 10^{12}$ cfu/per seed, about $1 \times 10^7$ to $1 \times 10^{13}$ cfu/per seed, about $1 \times 10^8$ to $1 \times 10^9$ cfu/per seed, about $1 \times 10^8$ to $1 \times 10^{10}$ cfu/per seed, about $1 \times 10^8$ to $1 \times 10^{11}$ cfu/per seed, about $1 \times 10^8$ to $1 \times 10^{12}$ cfu/per seed, about $1 \times 10^8$ to $1 \times 10^{13}$ cfu/per seed, about $1 \times 10^9$ to $1 \times 10^{10}$ cfu/per seed, about $1 \times 10^9$ to $1 \times 10^{11}$ cfu/per seed, about $1 \times 10^9$ to $1 \times 10^{12}$ cfu/per seed, about $1 \times 10^9$ to $1 \times 10^{13}$ cfu/per seed, about $1 \times 10^{10}$ to $1 \times 10^{11}$ cfu/per seed, about $1 \times 10^{10}$ to $1 \times 10^{12}$ cfu/per seed, about $1 \times 10^{10}$ to $1 \times 10^{13}$ cfu/per seed, about $1 \times 10^{11}$ to $1 \times 10^{12}$ cfu/per seed, about $1 \times 10^{11}$ to $1 \times 10^{13}$ cfu/per seed, and about $1 \times 10^{12}$ to $1 \times 10^{13}$ cfu/per seed. As used herein, the term "colony forming unit" or "cfu" is a unit containing entomopathogen fungal structures capable of growing and producing a colony in favorable conditions. The cfu count serves as an estimate of the number of viable structures or cells in a sample.

In an embodiment, an entomopathogenic fungal strain and/or a composition can be formulated as a liquid seed treatment comprising an entomopathogenic fungal strain and/or composition disclosed herein. The seeds are substantially uniformly coated with one or more layers of an entomopathogenic fungal strain, using conventional methods of mixing, spraying or a combination thereof. Application is done using equipment that accurately, safely, and efficiently applies a seed treatment product to a seed. Such equipment uses various types of coating technology such as rotary coaters, drum coaters, fluidized bed techniques, spouted beds, rotary mists or a combination thereof.

In an embodiment, an application is done via either a spinning "atomizer" disk or a spray nozzle that evenly distributes a seed treatment onto a seed as it moves through the spray pattern. In yet another embodiment, a seed is then mixed or tumbled for an additional period of time to achieve additional treatment distribution and drying. A seed can be primed or unprimed before coating with an entomopathogenic fungal strain and/or a composition disclosed herein to increase the uniformity of germination and emergence. In an alternative embodiment, a dry powder composition can be metered onto a moving seed.

In still another embodiment, a seed may be coated via a continuous or a batch coating process. In a continuous coating process, continuous flow equipment simultaneously meters both the seed flow and the seed treatment products. A slide gate, cone and orifice, seed wheel, or weight device (belt or diverter) regulates seed flow. Once the seed flow rate through treating equipment is determined, the flow rate of the seed treatment products is calibrated to the seed flow rate in order to deliver the desired dose to a seed as it flows through the seed treating equipment. Additionally, a computer system may monitor the seed input to the coating machine, thereby maintaining a constant flow of the appropriate amount of a seed.

In a batch coating process, batch treating equipment weighs out a prescribed amount of a seed and places the seed into a closed treating chamber or bowl where a corresponding amount of seed a treatment is then applied. The seed and the seed treatment are then mixed to achieve a substantially uniform coating on each seed. This batch is then dumped out of the treating chamber in preparation for the treatment of a next batch. With computer control systems, this batch process is automated enabling it to continuously repeat a batch treating process.

A variety of additives can be added to a seed treatment. Binders can be added and include those composed preferably of an adhesive polymer that can be natural or synthetic without phytotoxic effect on a seed to be coated. A variety of colorants may be employed, including organic chromophores classified as nitroso, nitro, azo, including monoazo, bisazo, and polyazo, diphenylmethane, triarylmethane, xanthene, methane, acridine, thiazole, thiazine, indamine, indophenol, azine, oxazine, anthraquinone, and phthalocyanine and combinations thereof. Other additives can be added including trace nutrients such as salts of iron, manganese, boron, copper, cobalt, molybdenum, and zinc and combinations thereof. A polymer or other dust control agent can be applied to retain a treatment on a seed surface.

Other conventional seed treatment additives include, but are not limited to, coating agents, wetting agents, buffering agents, and polysaccharides. An agriculturally acceptable carrier can be added to a seed treatment formulation such as water, solids or dry powders. A dry powder can be derived from a variety of materials such as wood barks, calcium carbonate, gypsum, vermiculite, talc, humus, activated charcoal, and various phosphorous compounds.

In an embodiment, a seed coating can comprise of a filler, which is an organic or an inorganic, a natural or a synthetic component with which an entomopathological fungal strain and/or a composition hereof is combined to facilitate its application onto a seed. In an embodiment, a filler is an inert solid such as clays, natural or synthetic silicates, silica, resins, waxes, solid fertilizers (for example ammonium salts), natural soil minerals, such as kaolins, clays, talc, lime, quartz, attapulgite, montmorillonite, bentonite, or diatomaceous earths, or synthetic minerals, such as silica, alumina, or silicates, in particular aluminum or magnesium silicates and combinations thereof.

In an embodiment, an entomopathogenic fungal strain and/or a composition disclosed herein may be formulated by encapsulation technology to improve fungal spore stability and as a way to protect the fungal spores from seed applied fungicides. In an embodiment the encapsulation technology may comprise a bead polymer for timed release of an entomopathogenic fungal strain and/or a composition disclosed herein over time. In an embodiment, the encapsulation technology may comprise a zeolite material. In an embodiment, an encapsulated entomopathogenic fungal strain and/or a composition disclosed herein may be applied in a separate application of beads in-furrow to the seeds. In another embodiment, an encapsulated entomopathogenic fungal strain and/or a composition disclosed herein may be co-applied along with seeds simultaneously.

Insect resistance management (IRM) is a term used to describe practices aimed at reducing the potential for insect pests to become resistant to an insect management tactic. Maintenance of the efficacy of a Bt (*Bacillus thuringiensis* derived pesticidal protein), another pesticidal protein, a chemical, or a biological agent is necessary for effective insect control. IRM is of great importance in maintaining effective insect control because of the threat insect resistance poses to the future use of pesticidal plant-incorporated protectants and insecticidal trait technology as a whole. Specific IRM strategies, such as a refuge strategy, mitigate insect resistance to specific insecticidal proteins produced in corn, soybean, cotton, and other crops. However, such strategies result in portions of crops being left susceptible to one or more insect pests in order to ensure that non-resistant insects develop and become available to mate with any resistant insect pests produced in a protected crop. Accordingly, from a farmer/producer's perspective, it is highly desirable to have as small a refuge as possible and yet still manage insect resistance, in order that the greatest yield is obtained while still maintaining the efficacy of the insect pest control method used, whether the method is a Bt pesticidal protein, a different pesticidal protein, a chemical, a biological agent, some other compound or method, or combinations thereof.

An often used IRM strategy is the planting of a refuge (a portion of the total acreage using non-Bt/pesticidal trait seed), as it is commonly-believed that this will delay the development of insect resistance to pesticidal traits by maintaining insect susceptibility. The theoretical basis of the refuge strategy for delaying resistance hinges on the assumption that the frequency and recessiveness of insect resistance is inversely proportional to insect pest susceptibility; resistance will be rare and recessive only when insect pests are very susceptible to a toxin, and conversely resistance will be more frequent and less recessive when insect pests are not very susceptible. Furthermore, the strategy assumes that resistance to an insecticidal trait is recessive and is conferred by a single locus with two alleles resulting in three genotypes: susceptible homozygotes (SS), heterozygotes (RS), and resistant homozygotes (RR). It also assumes that there will be a low initial resistance allele frequency and that there will be extensive random mating between resistant and susceptible adults. Under ideal circumstances, only rare RR individuals will survive a pesticidal toxin produced by a crop. Both SS and RS individuals will be susceptible to the pesticidal toxin. A structured refuge is a non-Bt/insecticidal trait portion of a grower's field or set of fields that provides for the production of susceptible (SS) insects that may randomly mate with rare resistant (RR) insects surviving the insecticidal trait crop, which may be a Bt trait crop, to produce susceptible RS heterozygotes that will be killed by the Bt/insecticidal trait crop. An integrated refuge is a certain portion of a grower's field or set of fields of randomly planted non-Bt/insecticidal trait plants that provides for the production of susceptible (SS) insects that may randomly mate with rare resistant (RR) insects surviving the insecticidal trait crop to produce susceptible RS heterozygotes that will be killed by the pesticidal trait crop. Each refuge strategy will remove resistant (R) alleles from an insect population and delay the evolution of resistance.

Another strategy to reduce the need for a refuge is the pyramiding of traits with different modes of action against a target pathogen, pest or insect. For example, Bt toxins that have different modes of action pyramided in one transgenic plant are able to have reduced refuge requirements due to reduced resistance risk. Different modes of action in a pyramid combination also extend the durability of each trait, as resistance is slower to develop to each trait.

Currently, the size, placement, and management of a refuge are often considered critical to the success of refuge strategies to mitigate insect resistance to a Bt/pesticidal trait produced in corn, cotton, soybean, and other crops. Because of the decrease in yield in refuge planting areas, some farmers choose to eschew the refuge requirements, and others do not follow the size and/or placement requirements. These issues result in either no refuge or a less effective refuge, and a corresponding risk of an increase in the development of resistant pests.

Accordingly, there remains a need for methods for managing pest resistance in a plot of pest resistant crop plants. It would be useful to provide an improved method for the protection of plants, especially corn and soybeans as well as other crop plants, from feeding damage by pests. It would be particularly useful if such a method reduced the required application rate of conventional chemical pesticides and insecticides, and limited the number of separate field operations required for crop planting and cultivation. In addition, a method of deploying a biocontrol agent that increases the durability of an insecticidal/pesticidal trait or increases the efficacy of a resistance management strategy would be useful.

An embodiment relates to a method of reducing or preventing the development of resistance to a plant insecticidal/pesticidal composition of a pest in a population of pests comprising providing a plant protection composition, such as a Bt insecticidal/pesticidal protein, a transgenic insecticidal/pesticidal protein, another pesticidal protein, a chemical pesticide, or a pesticidal biological agent, to seed, a plant, a plant part or a planted area or an insecticidal trait and providing an entomopathogenic fungal strain, and/or a composition, and/or a method described herein to the seed, the plant, the plant part or the planted area or the insecticidal trait. Another embodiment relates to a method of reducing or preventing the development of resistance to a plant pesticidal/insecticidal trait comprising providing a composition comprising a plant pesticidal/insecticidal trait and an entomopathogenic fungal strain and/or a composition described herein. A further embodiment relates to a method of reducing or preventing the development of resistance to a plant *Coleopteran* insecticidal trait comprising providing a composition comprising a plant *Coleopteran* insecticidal trait and an entomopathogenic fungal strain and/or a composition described herein. Another embodiment relates to a method of reducing or preventing the development of resistance to a plant *Diabrotica virgifera virgifera* insecticidal trait comprising providing a plant *Diabrotica virgifera virgifera* insecticidal trait and an entomopathogenic fungal strain and/or a composition described herein.

A further embodiment relates to a method of increasing the durability of plant pest compositions comprising providing a plant protection composition to a seed, a plant, a plant part or a planted area, and providing an entomopathogenic fungal strain, and/or a composition, and/or a method described herein to the seed, the plant, the plant part or the planted area, wherein the entomopathogenic fungal strain, and/or the composition, and/or the method described herein has a different mode of action than the plant protection composition.

In a still further embodiment, a required refuge may be reduced or eliminated by the presence of an entomopathogenic fungal strain, and/or a composition, and/or a method described herein when applied to a non-refuge plant. In another embodiment, a refuge may include an entomopathogenic fungal strain, and/or a composition, and/or a method described herein as a spray, a bait, or as a different mode of application.

In an embodiment of the invention, a composition that increases resistance to a pathogen, a pest, or an insect comprises an entomopathogenic fungal strain disclosed herein and a non-Bt insecticidal trait. In another embodiment, an entomopathogenic fungal strain is selected from the group consisting of: *Metarhizium anisopliae* 15013-1, *Metarhizium robertsii* 23013-3, and *Metarhizium anisopliae* 3213-1. In another embodiment, a non-Bt insecticidal trait comprises a plant-derived insecticidal protein, a bacterial/archeal-derived insecticidal protein not from a Bt (such as a *Pseudomonas* insecticidal protein), an animal-derived insecticidal protein, or a silencing element. In another embodiment of the invention, a composition that increases durability of a non-Bt insecticidal trait comprises an entomopathogenic fungal strain and a non-Bt insecticidal trait. In another embodiment, a non-Bt insecticidal trait comprises a PIP-72 polypeptide of PCT Serial Number PCT/US14/55128. In another embodiment, a non-Bt insecticidal trait comprises a polynucleotide silencing element targeting RyanR (US Patent Application publication 2014/0275208). In another embodiment, a non-Bt insecticidal trait comprises a polynucleotide silencing element targeting RyanR (US Patent Application publication 2014/0275208) and a PIP-72 polypeptide of PCT Serial Number PCT/US14/55128.

In a further embodiment, a composition that increases resistance to a pathogen, a pest, or an insect comprises an entomopathogenic fungal strain disclosed herein and a Bt insecticidal trait. These compositions may provide to a seed, a plant or a plant part additive or synergistic resistance to a pathogen, a pest, or an insect. A Bt insecticidal trait may have activity to *Coleopteran* plant pests, such as *Diabrotica virgifera virgifera*. In an embodiment of the invention, a composition comprises an entomopathogenic fungal strain disclosed herein and a Bt insecticidal trait, wherein the Bt insecticidal trait comprises a Cry3B toxin disclosed in U.S. Pat. No. 8,101,826, PCT Publications WO 2002/028184, WO 2002/030205, WO 2002/028185, and WO 2000/011185, a mCry3B toxin disclosed in U.S. Pat. No. 8,269,069 and PCT Publication WO 1999/031248, a mCry3A toxin disclosed in PCT Publication WO 2003/018810 and U.S. Pat. No. 8,269,069, or a Cry34/35 toxin disclosed in U.S. Pat. Nos. 7,309,785, 7,524,810, 7,985,893 and 7,939,651 and PCT Publication WO 2001/014417, and transgenic events containing these Bt insecticidal toxins and other Coleopteran active Bt insecticidal traits for example, event MON863 disclosed in PCT Publication WO 2004/011601, event MIR604 disclosed in PCT Publication WO 2005/103301, event 5307 disclosed in U.S. Pat. No. 9,133,474, event DAS-59122 disclosed in PCT Publication WO 2006/039376, event DP-4114 disclosed in PCT Publication WO 2013/147018, event MON 87411 disclosed in PCT Publication WO 2013/169923, and event MON88017 disclosed in PCT Publication WO 2005/059103 all of which are incorporated herein by reference.

The entomopathogenic fungal strains, compositions, and methods will be further understood by reference to the following non-limiting Examples. The following Examples are provided for illustrative purposes only. The Examples are included solely to aid in a more complete understanding of the described embodiments of the invention. The Examples do not limit the scope of the embodiments of the invention described or claimed.

Example 1

Growing *Metarhizium anisopliae* Strain 15013-1 in Liquid Culture at Shake Flask Scale Siliconized 4-baffle shake flasks with 50 mL of soy 10C (25% glucose+75% fructose):1N medium (Table 3) were inoculated with $5\times10^6$ AC/mL of *M. anisopliae* strain 15013-1 in duplicate. The culture was incubated at 300 rpm and 28° C. for 7 days, samples were taken at day 3, 5 and 7, and fermentation parameters recorded. At the end of the 7-day fermentation $6.825\times10^4$ Microsclerotia (MS)/mL$\pm0.849\times10^4$ MS/mL, $8.000\times10^7$ Submerged Spores (SS)/mL$\pm2.828\times10^7$ SS/mL, and DCW of 43.07 g/kg±2.91 g/kg were produced in the culture. In addition, a pH of 7.0±0 and glucose concentration of 54 mg/mL±16 mg/mL were recorded in the culture (FIG. 1 and Table 4).

TABLE 4

DCW, pH and glucose concentration at end of liquid fermentation of *M. anisopliae* strain 15013-1 in soy 10 C. (25% glucose + 75% fructose):1N medium after 7 days of incubation at 300 rpm and 28° C., at shake flask scale.

| *M. anisopliae* strain 15013-1 | Average | StDev |
|---|---|---|
| DCW [g/kg] | 43.07366 | 2.90557 |
| pH | 7 | 0 |
| Glucose [mg/L] | 54.00000 | 15.55635 |

Example 2

Growing *Metarhizium anisopliae* Strain 15013-1 in Liquid Culture at 2 L Benchtop Scale A siliconized 250 mL shake flask containing 50 mL of cottonseed 10C: 1N medium was inoculated with *M. anisopliae* strain 15013-1 aerial conidiospores (AC) at a final concentration of $5\times10^6$ AC/mL. The seed culture was grown at 28° C., 200 rpm for 2 days. After recording the MS and SS concentrations, 40 mL of the seed culture was inoculated into 1 L of Soy 10C:1N (25% glucose+75% fructose) medium. During production, 10% NaOH was used to prevent the pH from falling under pH 5.5. Agitation was started at 800 RPM, and was increased to maintain the DO above 30% with a maximum RPM of 1200. The temperature was 28° C. throughout the fermentation, and the length of the fermentation was 7 days. Various parameters were monitored during the fermentation and include, but were not limited to CER, DO, ammonia concentrations, pH, DCW, MS production, and SS production (FIGS. 2-5). At the end of fermentation, $1.368\times10^5$ MS/mL$\pm0.046\times10^5$ MS/mL, $7.000\times10^7$ SS/mL$\pm0.354\times10^7$ SS/mL, and DCW of 24.8 g/kg were produced in the culture.

Example 3

Growing *Metarhizium anisolpliae* Strain 15013-1 in Liquid Culture Bioreactor without Feeding A seed culture was started by inoculating 500 mL of cottonseed 10C:1N medium with *Metarhizium anisopilae* strain 15013-1 at a final concentration of $5\times10^6$ AC/mL. The seed cultures were incubated at 180 rpm and 28° C. for 2 days. A volume of 400 mL of the seed culture was mixed with 600 mL of sterile water and inoculated into each tank to bring the final volume to 10 L of soy 10C (25% glucose+75% fructose):1N medium. The production culture pH was controlled at pH 5.5 with NaOH for base addition and $H_2SO_4$ for acid addition. The pressure in the tank was set at 1 barg and the agitation was allowed to go up to a maximum of 850 RPM to maintain the dissolved oxygen of 20%. Various parameters were monitored during the fermentation and include, but were not limited to, CER, DO, ammonia concentrations, pH, DCW, MS production, and SS production (FIGS. 6-9). At the end of fermentation, $9.433\times10^4$ MS/mL$\pm1.366\times10^4$ MS/mL, $2.750\times10^7$ SS/mL$\pm1.061\times10^7$ SS/mL, and DCW of 25.0 g/kg were produced in the culture.

Growing *Metarhizium anisopliae* Strain 15013-1 in Liquid Culture Bioreactor with Carbon Source Feed A seed culture was started by inoculating 500 mL of cottonseed 10C:1N medium with *Metarhizium anisopilae* strain 15013-1 at a final concentration of $5\times10^6$ AC/mL. The seed cultures were incubated at 180 rpm and 28° C. for 2 days. A volume of 400 mL of the seed culture was mixed with 600 mL of sterile water and inoculated into each the tank to bring the final volume to 10 L of appropriate production medium. The production culture pH was controlled at pH 5.5 with NaOH for base addition and $H_2SO_4$ for acid addition. The pressure in the tank was set at 1 barg and the agitation was allowed to go up to a maximum of 850 RPM to maintain the dissolved oxygen of 20%. At 88.5 h, water was added to the tank in an attempt to loosen up the broth and clear some of the material on the head plate to allow for base to be added for pH control. A 50% (w/w) fructose solution was fed after the initial glucose and fructose was exhausted. Various parameters were monitored during the fermentation and include, but were not limited to, CER, DO, ammonia concentrations, pH, DCW, MS production, and SS production (FIGS. 10-13). At the end of fermentation, $1.928\times10^5$ MS/mL$\pm0.074\times10^5$ MS/mL, $6.250\times10^6$ SS/mL$\pm1.768\times10^6$ SS/mL, and DCW of 38.1 g/kg were produced in the culture.

Growing *Metarhizium anisopliae* Strain 15013-1 to Enrich for Submerged Spore Production in Liquid Culture Bioreactor A seed culture was started by inoculating 500 mL of cottonseed 10C:1N medium with *Metarhizium anisopilae* strain 15013-1 at a final concentration of $5 \times 10^6$ AC/mL. The seed culture was incubated at 100 rpm and 28° C. for 2 days. A volume of 400 mL of the seed culture was mixed with 600 mL of sterile water and inoculated into each the tank to bring the final volume to 10 L of soy 10C (25% glucose+75% fructose):1N medium. The production culture pH was controlled at pH 5.5 with NaOH for base addition and $H_2SO_4$ for acid addition. The agitation was set at 350 RPM and the dissolved oxygen was allowed to drop. This reduction in agitation created a stress condition, most likely a reduction in availability of oxygen, which resulted in an increase in the production of submerged spores during the production fermentation. Various parameters were monitored during the run and include, but were not limited to, CER (carbon dioxide evolution rate), OUR (oxygen uptake rate), DO (dissolved oxygen), pH, DCW (dry cell weight), microsclerotia (MS) concentration, and submerged spore (SS) concentration (FIGS. 14-17). At the end of fermentation, $4.500 \times 10^3$ MS/mL$\pm 1.146 \times 10^3$ MS/mL, $4.294 \times 10^8$ SS/mL$\pm 0.186 \times 10^8$ SS/mL, and DCW of 50.8 g/kg were produced in the culture.

All publications, patents and patent applications mentioned in the specification indicate the level of those skilled in the art to which this disclosure pertains. All publications, patents and patent applications are incorporated by reference to the same extent as if each individual publication, patent or patent application was specifically and individually indicated to be incorporated by reference.

Although the foregoing disclosure has been described in some detail by way of illustration and example for purposes of clarity of understanding, certain changes and modifications may be practiced within the scope of the appended claims.

What is claimed is:

1. A method of producing a fungal entomopathogenic product comprising:
   a. obtaining aerial conidiospores of a fungal entomopathogen selected from the group consisting of: *Metarhizium anisopliae* 15013-1, *Metarhizium robertsii* 23013-3, and *Metarhizium anisopliae* 3213-1;
   b. inoculating the aerial conidiospores into a liquid medium to generate a fungal entomopathogenic seed culture by fermentation; and
   c. inoculating the fungal entomopathogen seed culture into the liquid medium to generate a fungal entomopathogenic product by fermentation, wherein the liquid medium comprises a first carbon source, a second carbon source, and a nitrogen source.

2. The method of claim 1, further comprising obtaining the fungal entomopathogenic product from the liquid medium.

3. The method of claim 2, wherein obtaining the fungal entomopathogenic product from the liquid medium comprises vacuum drying.

4. The method of claim 1, wherein the first carbon source is in a limiting concentration to facilitate a non-optimal or stress condition of the fungal entomopathogen, wherein the non-optimal or stress condition results in conversion of the fungal entomopathogen to microsclerotia.

5. The method of claim 4, wherein the first carbon source comprises 10 to 35 percent by weight/volume of the total medium.

6. The method of claim 1, wherein the second carbon source is in a non-limiting concentration.

7. The method of claim 1, wherein the second carbon source creates a non-optimal or stress condition of the fungal entomopathogen, wherein the non-optimal or stress condition results in conversion of the fungal entomopathogen to microsclerotia.

8. The method of claim 1, wherein the first carbon source comprises a glucose molecule.

9. The method of claim 1, wherein the second carbon source comprises a fructose, a galactose, a sorbitol, a sorbose, a sucrose, an arabinose, a maltodextrin, a ribose, or a xylose molecule.

10. The method of claim 1, further comprising adjusting a fermentation parameter to create a non-optimal or stress condition that results in a change of a physiological state of the fungal entomopathogen, wherein the non-optimal or stress condition results in conversion of the fungal entomopathogen to microsclerotia.

11. The method of claim 1, wherein obtaining aerial conidospores of a fungal entomopathogen comprises first generating aerial conidiospores of the fungal entomopathogen on agar media or solid state media.

12. The method of claim 1, wherein the fungal entomopathogenic product comprises a spore, a conidiospore, a blastospore, an aerial conidiospore, a submerged conidiospore, a submerged blastospore, and/or a microsclerotium.

* * * * *